US009835618B1

(12) United States Patent
Swanson et al.

(10) Patent No.: US 9,835,618 B1
(45) Date of Patent: Dec. 5, 2017

(54) DISCOVERY, DETECTION AND USE OF BIOMARKERS

(75) Inventors: Basil I. Swanson, Los Alamos, NM (US); Harshini Mukundan, Los Alamos, NM (US); Rama Murthy Sakamuri, Los Alamos, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 1471 days.

(21) Appl. No.: 13/529,847

(22) Filed: Jun. 21, 2012

Related U.S. Application Data

(63) Continuation-in-part of application No. 12/658,298, filed on Feb. 8, 2010, now abandoned.

(60) Provisional application No. 61/206,980, filed on Feb. 6, 2009, provisional application No. 61/251,605, filed on Oct. 14, 2009, provisional application No. 61/499,665, filed on Jun. 21, 2011.

(51) Int. Cl.
*G01N 33/53* (2006.01)
*G01N 21/77* (2006.01)

(52) U.S. Cl.
CPC ......... *G01N 33/53* (2013.01); *G01N 21/7703* (2013.01)

(58) Field of Classification Search
None
See application file for complete search history.

(56) References Cited

U.S. PATENT DOCUMENTS

| | | | |
|---|---|---|---|
| 5,082,664 A * | 1/1992 | Lenk | A61K 9/127 264/4.3 |
| 7,190,851 B2 | 3/2007 | Grace et al. | |
| 2004/0241176 A1* | 12/2004 | Lamparski | A61K 39/0011 424/185.1 |
| 2011/0008798 A1 | 1/2011 | Mukundan et al. | |
| 2014/0295407 A1 | 10/2014 | Swanson et al. | |

OTHER PUBLICATIONS

Mukundan et al., Waveguide-Based Biosensors for Pathogen Detection, Sensors, 9, (2009), p. 5783-5809.*
Ernst et al., Molecular Interaction of CD1b with Lipoglycan Antigens, Immunity, 8,(1998), p. 331-340.*
Abreu et al., Binding of a Fluorescent lipid amphiphile to albumin and its transfer to lipid bilayer membranes, Biophysical Journal, (2003), 84, p. 386-399.*
Mukundan et al., "Waveguide-Based Biosensors for Pathogen Detection," *Sensors* 9:5783-5809, 2009.
Whiles et al., "Bicelles in structure-function studies of membrane-associated proteins," *Bioorg Chem* 30:431-442, 2002.
Mukundan et al., "Waveguide-based Optical Biosensor for the Detection of Tuberculosis-Specific Antigens in Patient Urine," poster presentation at the *Keystone Symposium on Tuberculosis and HIV*, 2008.
Mukundan et al., "Rapid detection of *Mycobacterium tuberculosis* biomarkers in a sandwich immunoassay format using a waveguide-based optical biosensor," *Tuberculosis* 92:407-416, 2012.
Akira et al., "Pathogen Recognition and Innate Immunity," *Cell* 124:783-801, 2006.
Daghastanli et al., "Lipid composition-dependent incorporation of multiple membrane proteins into liposomes," *Colloids Surf B Biointerfaces* 36(3-4):127-137, 2004.
Erridge et al., "The Induction of Colitis and Ileitis in Mice Is Associated with Marked Increases in Intestinal Concentrations of Stimulants of TLRs 2, 4 and 5," *PLoS ONE* 5(2):e9125, 2010.
Olguin et al., "Detection of flagellin by interaction with human recombinant TLR5 immobilized in liposomes," *Anal Bioanal Chem* 405:1267-1281, 2013.
Rigaud and Lévy, "Reconstitution of Membrane Proteins into Liposomes," *Methods Enzymol* 372:65-86, 2003.
Salazar et al., "Coevolution of Markers of Innate and Adaptive Immunity in Skin and Peripheral Blood of Patients with Erythema Migrans," *J Immunol* 171:2660-2670, 2003.
Tanaka and Sackmann, "Polymer-supported membranes as models of the cell surface," *Nature* 437(7059):656-663, 2005.
Anderson et al., "Functional PEG-modified thin films for biological detection," *Langmuir* 24(5):2240-2247, 2008.
Martinez et al., "Pathogen detection using single mode planar optical waveguides," *J Mater Chem* 15:4639-4647, 2005.
Mukundan et al., "Optimizing a waveguide-based sandwich immunoassay for tumor biomarkers: evaluating fluorescent labels and functional surfaces," *Bioconjug Chem* 20(2):222-230, 2009.
Noormohamed et al., "Detection of Lipopolysaccharides in Serum using a Waveguide-Based Optical Biosensor," *Proc. of SPIE*, vol. 10072, 2017.
Sakamuri et al., "Association of Lipoarabinomannan with High Density Lipoprotein in Blood: Implications for Diagnostics," *Tuberculosis*, vol. 93:301-307, 2013.
Shi et al., "SNARE Proteins: One to Fuse and Three to Keep the Nascent Fusion Pore Open," *Science* 335(6074):1355-1359, 2012.
Stromberg et al., "Membrane Insertion for the Detection of Lipopolysaccharides: Exploring the Dynamics of Amphiphile-in-Lipid Assays," *PLoS ONE*, vol. 11:e0156295, 2016.

(Continued)

*Primary Examiner* — Ram R Shukla
*Assistant Examiner* — Ellen J Marcsisin
(74) *Attorney, Agent, or Firm* — Klarquist Sparkman, LLP

(57) ABSTRACT

Provided herein are systems for and methods of capturing, detecting, quantifying, and characterizing target moieties that are characterized by having a lipophilic portion of sufficient size and chemical composition whereby the target moiety inserts (or partitions) into a lipid assembly. Examples of such assays employ synthetic lipid constructs such as supported bilayers which are used to capture target moieties; other example assays exploit the natural absorption of compounds into natural lipid constructs such as HDL or LDL particles or cell membranes to capture target moieties. In specific embodiments, the target moieties are bacterial pathogen associated molecular pattern (PAMP) molecules or compounds not yet identified as PAMP molecules. Also provided are methods of determining PAMP molecule fingerprints and profiles that are linked to (indicative of) bacterial infection, disease states or progression, development of antibiotic resistance, and so forth, as well as these fingerprints, profiles and methods of using them.

10 Claims, 12 Drawing Sheets

(56) References Cited

OTHER PUBLICATIONS

Vu et al., "Detection of Lipomannan in Cattle Infected with Bovine Tuberculosis," *Anal Sci*, vol. 33:457-460, 2017.

* cited by examiner

DISCOVERY, DETECTION AND USE OF BIOMARKERS

CROSS REFERENCE TO RELATED APPLICATIONS

This is a continuation-in-part of U.S. application Ser. No. 12/658,298, filed Feb. 8, 2010 now abandoned, which claims the benefit of U.S. Provisional Application No. 61/206,980, filed Feb. 6, 2009 and U.S. Provisional Application No. 61/251,605, filed Oct. 14, 2009. Applicants also claim the benefit of the earlier filing date of U.S. Provisional Application No. 61/499,665 filed on Jun. 21, 2011. The entire disclosure of each of the above-listed applications is incorporated herein by reference.

ACKNOWLEDGMENT OF GOVERNMENT SUPPORT

This invention was made with government support under Contract No. DE-AC52-06NA25396 awarded by the United States Department of Energy. The government has certain rights in the invention.

FIELD

The technology described herein relates to methods and systems for capture, identification, characterization, and/or quantification of target moieties (and mixtures or collections thereof) capable of partitioning into a lipid structure (e.g., containing a portion or domain with lipophilic character and/or a membrane spanning peptide); in some embodiments, the target moiety(s) is a biomarker.

BACKGROUND

Genomics and proteomics research has identified biomarkers that can be used in the detection and treatment of many diseases. Disease assessment can be based on one or many biomarkers, and in some cases, different biomarkers may be appropriate for different disease stages. Such biomarkers can be used to assess disease progress and aid in determining treatment as well as in judging the effectiveness of a course of treatment. Accordingly, biomarker-based measurements permit improved patient care and inform about control of infection and disease spread.

Unfortunately, biomarker-based measurements can be slow, expensive, or otherwise impractical. Conventional methods used with biomarkers are typically based on gel electrophoresis, enzyme-linked immunosorbent assays (ELISAs), plasma resonance, or other techniques. These methods generally have limited sensitivity, slow response, and lack specificity. Thus, although biomarkers offer promise for improved disease treatment and diagnosis, these advantages have not been realized in practice.

The outbreak of new infectious diseases (e.g., SARS and avian influenza), and the emergence of drug resistant forms of old diseases (e.g., *Staphylococcus aureus* and *Mycobacterium tuberculosis*, M. tb) have heightened the need for global infectious disease surveillance as a tool to control the spread of infection, and guide therapeutic intervention. Tuberculosis (TB), a manageable disease only 20 years ago, has reemerged with alarming increases in mortality due to new drug resistant strains and co-infection with HIV. Technologies are needed to enable high throughput global surveillance of TB and other diseases; such surveillance would facilitate, for instance, accurate diagnosis of active infection and emergence of drug resistance.

SUMMARY

Provided herein are methods for detecting, identifying, and characterizing target moieties such as amphiphilic or protein biomarkers of disease, including but not limited to bacterial pathogen-associated molecular patterns (PAMPs). Two broad types of assay methods are provided: (1) Assays in which target moieties are captured from a sample using a lipid assembly (such as a synthetic lipid construct) that is brought into contact or exposed to the sample, allowing target moieties with certain characteristics to insert (partition) at least partially into the lipid assembly, then the lipid assembly/target moiety complex is harvested and further analysis can take place; and (2) Assays in which naturally occurring lipid assemblies (e.g., HDL or LDL particles, cell membranes, etc.) that are already in contact with the target moieties are harvested, with the targeting moieties already inserted/embedded (partitioned) therein, followed by further analysis.

Also provided are methods of determining PAMP fingerprints and profiles that are linked to (e.g., indicative of) bacterial infection, disease states, disease progression, development of antibiotic resistance, and so forth, as well as these fingerprints, profiles and methods of using them.

The foregoing and other objects, features, and advantages will become more apparent from the following detailed description, which proceeds with reference to the accompanying figures.

DETAILED DESCRIPTION

I. Abbreviations

Figure 1A:
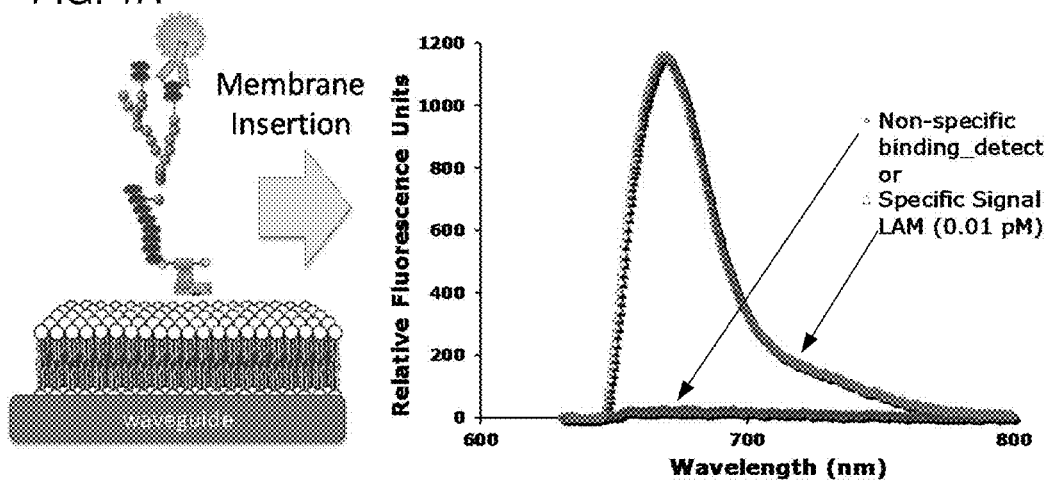
FIG. 1A is a schematic depiction of membrane insertion (left panel) and data showing detection of 10 fM lipoarabinomannan (LAM; right panel).

Apo apolipoprotein
CEA carcinoembryonic antigen
CFP-10 Culture Filtrate Protein 10
CL Cardiolipin
CMV cytomegalovirus
CRP C-reactive protein
DAMP danger-associated molecular patterns
EBV Epstein-Barr virus
ELAM endothelial cell-leukocyte adhesion molecule
ELISA enzyme-linked immunosorbent assay
ESAT-6 early secretory antigen 6
HDL high density lipoprotein
HTLN high-throughput laboratory network
LAM lipoarabinomannan
LDL low density lipoprotein
LPS lipopolysaccharide
LRR leucine-rich repeats
MDR multi-drug resistant
NBS nucleotide binding site
NOD nucleotide-binding oligomerization domain protein
PAMP pathogen-associated molecular pattern
PGL-I phenolic glycolipid 1
PGN peptidoglycan
SAM self-assembling monolayer
SAP serum amyloid P component
SCA single chain antibody
SEAP secreted alkaline phosphatase
SLB supported lipid bilayer
SNP single nucleotide polymorphisms
TB tuberculosis
t-BLM tethered bilayer lipid membrane
TLR Toll-like receptor
XDR extensively drug-resistant II. Terms Definitions of common terms in molecular biology may be found in Benjamin Lewin, Genes V, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the invention, the following explanations of specific terms are provided:

Affinity Molecule or Affinity Ligand: A ligand/molecule that binds a selected target molecule/moiety specifically and reversibly. Antibodies are one example of an affinity molecule, which selectively bind the antigen to which they were raised. The biotin/streptavidin pair is another example.

Amphipathic: An amphipathic molecule contains both lipophilic/hydrophobic (non-polar) and lipophobic/hydrophilic (polar) groups/moieties. Such a compound is called amphiphilic or an amphiphile. The lipophilic portion of an amphipathic compound is able to insert at least partially into a lipid structure, such as a lipid bilayer, monolayer, micelle, or vesicle.

Without intending to be bound to any particular structure, the hydrophobic group in an amphiphile may be an alkyl group, such as a long carbon chain, for example, with the formula: $CH_3(CH_2)_n$, (where n is generally greater than or equal to about 4 to about 16). Such carbon chains also optionally comprise one or more branches, wherein one hydrogen is replaced with an aliphatic moiety, such as an alkyl group. A hydrophobic group also can comprise an aryl group. The hydrophilic group/portion of an amphiphile comprises one or more of the following: a peptide or protein, a carbohydrate, an ionic molecule, such as an anionic molecule (e.g., a fatty acid, a sulfate or a sulfonate) or a cationic molecule, an amphoteric molecule (e.g., a phospholipid), or a non-ionic molecule (e.g., a small polymer). One of ordinary skill in the art will understand that the term amphiphile encompasses myriad different combinations of hydrophilic (water soluble) and hydrophobic (lipid soluble) moieties. In some embodiments herein, the amphiphile is a large amphiphile such as LAM, LPS or lipomannan. In other embodiments, the amphiphile is a small amphiphile such as PGL-I or mycobactin T.

Antibody: A polypeptide ligand comprising at least a light chain or heavy chain immunoglobulin variable region which specifically recognizes and binds an epitope (e.g., an antigen). This includes intact immunoglobulins and the variants and portions of them well known in the art, such as Fab' fragments, F(ab)'$_2$ fragments, single chain Fv proteins ("scFv"), disulfide stabilized Fv proteins ("dsFv"), diabodies (dimers of scFv fragments), and minibodies (fusions of scFv and CH3 domain). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (e.g., humanized murine antibodies), heteroconjugate antibodies (e.g., bispecific antibodies). See also, *Pierce Catalog and Handbook*, 1994-1995 (Pierce Chemical Co., Rockford, Ill.); Kuby, J., *Immunology*, 3$^{rd}$ Ed., W.H. Freeman & Co., New York, 1997.

Typically, an immunoglobulin has a heavy and light chain. Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs". The extent of the framework region and CDRs has been defined according to Kabat et al. (see, Kabat et al., *Sequences of Proteins of Immunological Interest*, U.S. Department of Health and Human Services, 1991) and the ImMunoGeneTics database (IMGT) (see, Lefranc, *Nucleic Acids Res* 29:207-9, 2001). The Kabat and IMGT databases are maintained online. The sequences of the framework regions of different light or heavy chains are relatively conserved within a species. The framework region of an antibody, that is the combined framework regions of the constituent light and heavy chains, serves to position and align the CDRs in three-dimensional space.

CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found.

References to "$V_H$" or "VH" refer to the variable region of an immunoglobulin heavy chain, including that of an Fv, scFv, dsFv or Fab. References to "$V_L$" or "VL" refer to the variable region of an immunoglobulin light chain, including that of an Fv, scFv, dsFv or Fab.

A "monoclonal antibody" is an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

A "humanized" immunoglobulin is an immunoglobulin including a human framework region and one or more CDRs from a non-human (such as a mouse, rat, or synthetic) immunoglobulin. The non-human immunoglobulin providing the CDRs is termed a "donor," and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, i.e., at least about 85-90%, such as about 95% or more identical. Hence, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Humanized immunoglobulins can be constructed by means of genetic engineering (e.g., see U.S. Pat. No. 5,585,089).

Biological Sample: Any biological material, such as a fluid produced from or obtained from an organism, a cell, a collection of cells (e.g., cultured cells), a tissue sample, a biopsy, or an organism. Biological samples also include blood and blood products (e.g., plasma) and other biological fluids (e.g., tears, sweat, sputum, saliva and related fluids, urine, tears, mucous, and so forth). Tissue samples can be from any organ or tissue in the body, including heart, liver, muscle, adipose, brain, lung, testes, and brain.

Biological samples may be from individual subjects (e.g., animals, such as humans, mice, rats, monkeys, marmosets, chickens, cats, dogs, pigs, guinea pigs, horses, cows, fruit flies, or worms) and/or archival repositories. The samples may be acquired directly from the individuals, from clinicians (for instance, who have acquired the sample from the individual), or directly from archival repositories.

Figure 3A:
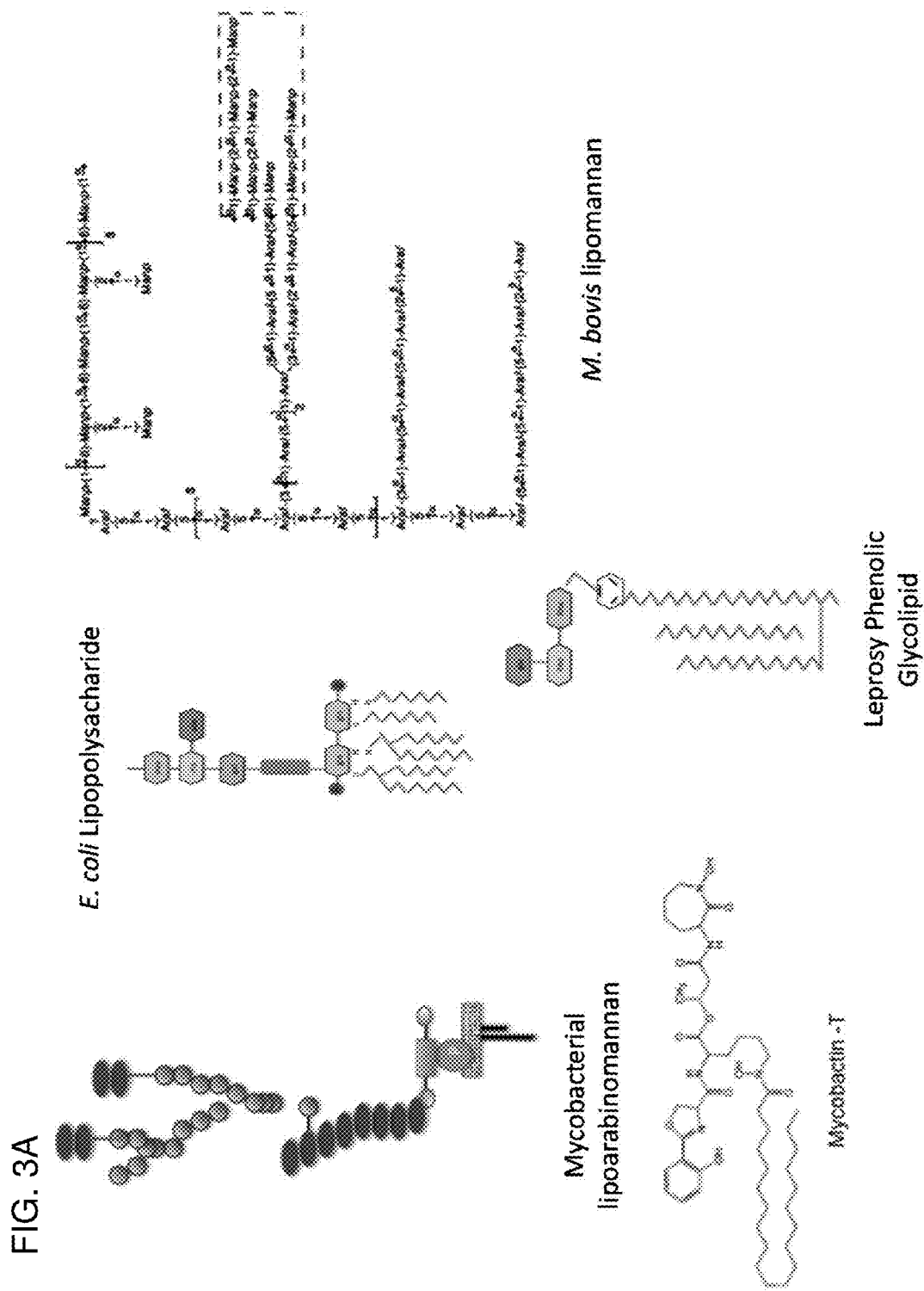
FIG. 3A shows representative amphiphilic biomarkers of disease detectable by membrane insertion, including Mycobacterial lipoarabinomannan, mycobactin T, lipopolysaccharide (LPS), phenolic glycolipid (PGL) from *M. leprae* and lipomannan from *M. bovis*.
Figure 3B:
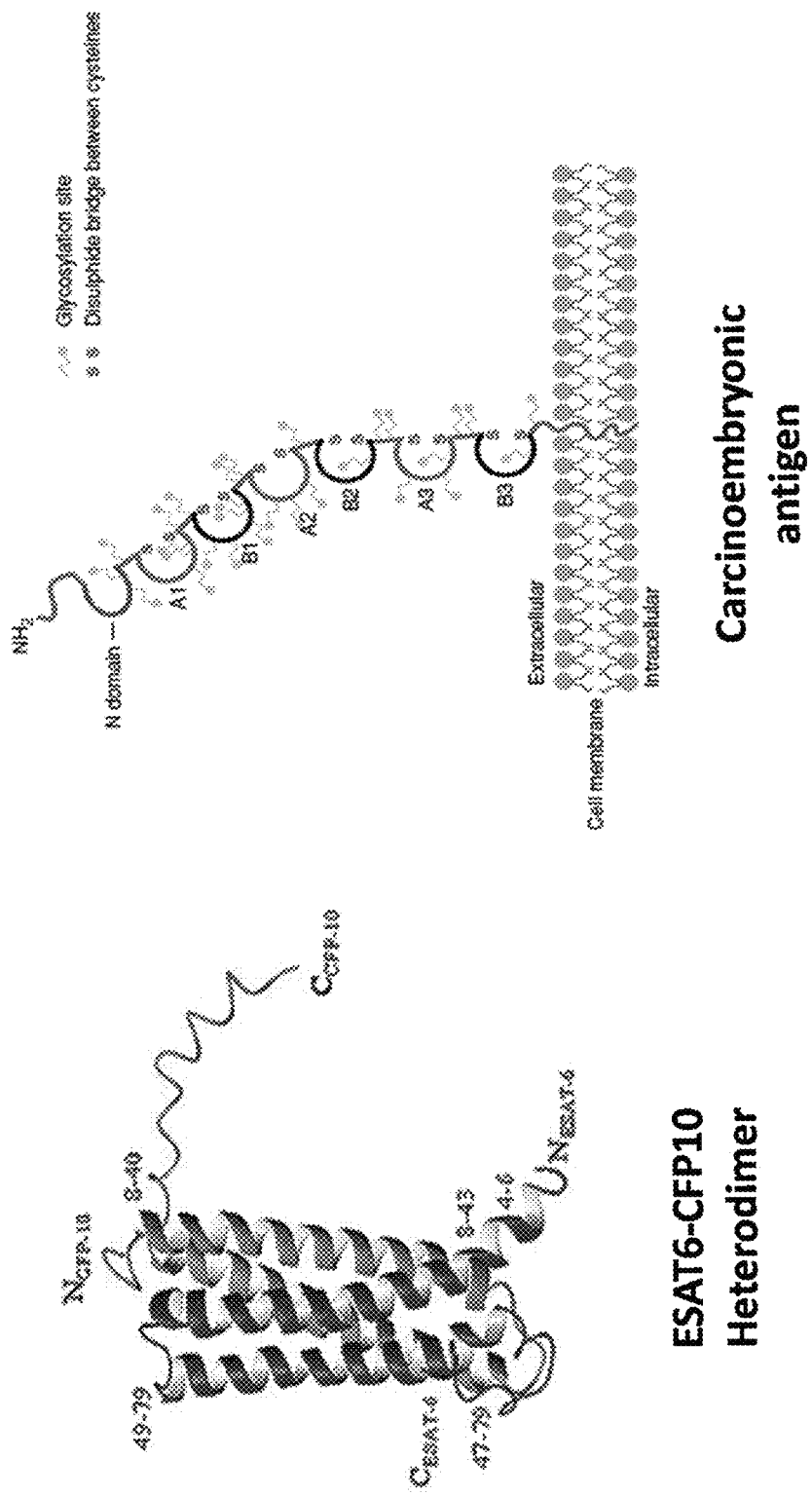
FIG. 3B shows representative protein biomarkers of disease detectable by membrane insertion, including CFP10 (shown as a heterodimer with ESAT6) and carcinoembryonic antigen (CEA).

Biomarker: A substance (or set of substances) used as an indicator of a biological state, most commonly a disease. In many instances, biomarkers are biomolecules that are differentially expressed during the course of disease. In the case of infectious disease, example biomarkers are pathogen-associated biomolecules that are secreted in the host during infection. Many biomarkers are virulence factors required for pathogenicity of the infectious agent and several are expressed very early in disease onset. By way of example, some disease biomarkers (such as for tuberculosis, leprosy and cancer) are shown in FIG. 3A and FIG. 3B.

Cardiolipin: (IUPAC name: 1,3-bis(sn-3'-phosphatidyl)-sn-glycerol) An important component of the inner mitochondrial membrane, where it constitutes about 20% of the total lipid composition. The name 'cardiolipin' is derived from the fact that it was first identified in animal hearts. Cardiolipin (CL) is essential for the optimal function of numerous enzymes that are involved in mitochondrial energy metabolism.

Culture Filtrate Protein 10 (CFP-10): The protein encoded by the esxB gene, CFP-10 is a 10 kDa antigen secreted from *Mycobacterium tuberculosis*. It forms a 1:1 heterodimeric complex with ESAT-6. Both genes are expressed from the RD1 region of the bacterial genome and play a key role in the virulence of the infection. CFP-10 is also known as ESAT-6-like protein esxB or secreted antigenic protein MTSA-10. See FIG. 3B.

Early Secretory Antigen 6 (ESAT-6): ESAT-6 is a 6 kDa early secretory antigenic target of *Mycobacterium tuberculosis*. ESAT-6 forms a 1:1 heterodimeric complex with CFP-10. It is a potent T cell antigen, and is used in tuberculosis diagnosis by the whole blood interferon γ test QuantiFERON-TB Gold (QFT), in conjunction with CFP-10 and TB7.7.

Flagellin: The basic element of bacterial flagella, surface structures on bacteria (such as gram negative bacteria) that are involved in motility. Flagellin has a molecular weight of approximately 40,000 daltons, and is composed of subunits arranged in several-stranded helix formation somewhat resembling myosin in structure. Exemplary flagellin proteins are described, for example, in U.S. Pat. Nos. 6,585,980; 6,130,082; 5,888,810; 5,618,533; and 4,886,748; U.S. Patent Publication No. US 2003/0044429; and Donnelly et al., *J. Biol. Chem.* 43: 40456, 2002, all incorporated herein by reference. Natural flagellin includes (i) a flagellin N-terminal constant region; (ii) a flagellin C-terminal constant region; and (iii) a flagellin hypervariable region between the two constant regions.

Hydrophobic: A hydrophobic (or lipophilic) group is electrically neutral and nonpolar, and thus prefers other neutral and nonpolar solvents or molecular environments. Examples of hydrophobic molecules include alkanes, oils and fats.

Hydrophilic: A hydrophilic (or lipophobic) group is electrically polarized and capable of H-bonding, enabling it to dissolve more readily in water than in oil or other "nonpolar" solvents.

Infectious disease: Any disease caused by an infectious agent. Examples of infectious pathogens include, but are not limited to: viruses, bacteria, *mycoplasma* and fungi. In a particular example, it is a disease caused by at least one type of infectious pathogen. In another example, it is a disease caused by at least two different types of infectious pathogens. Infectious diseases can affect any body system, be acute (short-acting) or chronic/persistent (long-acting), occur with or without fever, strike any age group, and overlap each other. Infectious diseases can be opportunistic infections, in that they occur more frequently in immunocompromised subjects Examples of infectious bacteria include: *Helicobacter pylori, Borelia burgdorferi, Legionella* sps including *Legionella pneumophilia, Mycobacteria* sps (such as. *M. tuberculosis, M. avium, M. bovis, M. intracellulare, M. kansaii, M. gordonae, M. leprae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (*viridans* group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus anthracis, corynebacterium diphtheriae, corynebacterium* sp., *Erysipelothrix rhusiopathiae, Escherichia coli, Clostridium perfringers, Clostridium tetani, Enterobacter aerogenes, Klebsiella pneumoniae, Pasteurella multocida, Bacteroides* sp., *Fusobacterium nucleatum, Streptobacillus moniliformis, Treponema pallidum, Treponema pertenue, Leptospira, Actinomyces israelli, Vibrio cholerae, Yersinia pestis, Mycobacterium leprae, Salmonella typhimurium, Campylobacter jejuni, Helicobacter pylori, Haemophilus* influenza, and *Pseudomonas* sps. Also contemplated are gram negative bacteria having lipopolysaccharide and any gram positive bacteria having lipoteichoic acid.

Label: A detectable compound or composition that is conjugated directly or indirectly to another molecule (such as a nucleic acid molecule or protein, for instance an antibody) to facilitate detection of that molecule. Examples of labels include, but are not limited to, radioactive isotopes, enzyme substrates, co-factors, ligands, chemiluminescent agents, fluorophores, haptens, enzymes, and combinations thereof. Methods for labeling and guidance in the choice of labels appropriate for various purposes are discussed for example in Sambrook et al. (Molecular Cloning: A Laboratory Manual, Cold Spring Harbor, N.Y., 1989) and Ausubel et al. (In Current Protocols in Molecular Biology, John Wiley & Sons, New York, 1998).

Lipid: As used herein, the term lipid refers to a class of water-insoluble, oily or greasy organic substances that are extractable from cells and tissues by nonpolar solvents, such as chloroform or ether. The most abundant kinds of lipids are fats or triacylglycerols, which are major fuels for most organisms. Another class of lipids is the polar lipids, which are major components of cell membranes. The following table (Table 1) provides one way (by chemical structure) of grouping major types of lipids:

TABLE 1

| Lipid type | Representative examples or sub-groups |
|---|---|
| Triacylglycerols | |
| Waxes | |
| Phosphoglycerides | phosphatidylethanolamine |
| | phosphatidylcholine |
| | phosphatidylserine |
| | phosphatidylinositol |
| | cardiolipin |
| Sphingolipids | sphingomyelin |
| | cerebrosides |
| | gangliosides |
| Sterols and their fatty acid esters | (see Table 3) |

Lipids may also be broken down into other recognized classes, such as those shown in Table 2.

TABLE 2

| SCIENTIFIC NAME | ABBREVIATION |
|---|---|
| Lyso-Phosphatidylcholine | LY |
| Sphingomyelin | SP |
| Phosphatidylcholine | PC |
| Phosphatidylserine | PS |
| Phosphatidylinositol | PI |
| Phosphatidylethanolamine | PE |
| Cardiolipin | CL |
| Free Fatty Acids | FFA |
| Monoacylglycerides | MAG |
| Diacylglycerides | DAG |
| Triacylglycerides | TAG |
| Cholesterol Esters | CE |
| Phosphatidic acids | PA |
| Phosphatidylglycerols | PG |
| CDP-diacylglycerols | CDP-DAG |
| Lysocardiolipin | LyCL |
| Lysophosphatidylethanolamine | LyPE |

Also included in the term lipid are the compounds collectively known as sterols. Table 3 shows representative sterols.

TABLE 3

| SCIENTIFIC NAME | MOLECULAR FORMULA | COMMON NAME |
|---|---|---|
| 5b-cholestan-3b-ol | $C_{27}H_{48}O$ | coprostanol |
| 5a-cholestan-3b-ol | $C_{27}H_{48}O$ | dihydrocholesterol |
| 5-cholesten-3b-ol | $C_{27}H_{46}O$ | cholesterol |
| 5,24-cholestadien-3b-ol | $C_{27}H_{44}O$ | desmosterol |
| 5-cholestan-25a-methyl-3b-ol | $C_{28}H_{42}O$ | campesterol |
| 5-cholestan-24b-methyl-3b-ol | $C_{28}H_{42}O$ | dihydrobrassicasterol |
| 5-cholesten-24b-ethyl-3b-ol | $C_{29}H_{50}O$ | b-sitosterol |
| 5,22-cholestadien-24b-ethyl-3b-ol | $C_{29}H_{48}O$ | stigmasterol |

Lipid A: A lipid component of an endotoxin responsible for toxicity of Gram-negative bacteria. It is the innermost of the three regions of a lipopolysaccharide (LPS, also called endotoxin) molecule; its hydrophobic nature allows it to anchor the LPS to the outer membrane (Raetz & Whitfield, *Annu Rev. Biochem* 71(1)635-700, 2002). While its toxic effects can be damaging, the sensing of lipid A by the immune system may also be important for the onset of immune responses to Gram-negative infection, and for the subsequent successful fight against the infection.

Lipid assembly: A broad term that encompasses all structures that include lipid molecules, including particularly mono-layers and bi-layers, substantially planar structures, vesicles (unilamellar or multilamellar, liposomes, micelles, nanodiscs, and bicelles, for instance. Also included in this term are supported lipid bilayers (SLB), tethered bilayer lipid membranes (t-BLM), and self-assembled monolayers (SAM), as well as naturally occurring or synthetic HDL particles, naturally occurring or synthetic LDL particles, or a mixture of any two or more of any of these.

The term "lipid assembly" encompasses naturally occurring lipid structures (e.g., HDL or LDL particles extracted from blood, cell membranes, and so forth), as well as synthetic lipid constructs, both planar and vesicular and otherwise, whether made from purified lipidic compounds or defined or undefined mixtures of lipidic compounds.

Lipoarabinomannan (LAM): Lipoarabinomannan is a lipoglycan (a lipid to which a carbohydrate is attached) and major virulence factor in the bacterial genus *Mycobacterium*, including *M. tuberculosis*. LAM is illustrated in FIG. 3A.

Lipopeptide: A molecule comprising both a peptide moiety and at least one lipid (acyl) moiety. Many microbial species contain in their inner and outer membranes and/or cell walls amphipathic lipids based on one or two amino acids linked to one (monoacyl), two (diacyl) or three (triacyl) fatty acids. Diacyl lipopeptides and triacyl lipopeptides are known PAMPs recognized by TLRs.

Lipophilic: The term lipophilic refers to the ability of a chemical compound to insert into (partition into) a lipid structure such as a lipid bi-layer; a lipophilic compound can dissolve in fats, oils, lipids, and non-polar solvents such as hexane or toluene. Lipophilic substances interact within themselves and with other substances through the London dispersion force. They have little to no capacity to form hydrogen bonds. When a molecule of a lipophilic substance is enveloped by water, surrounding water molecules enter into an ice-like structure over the greater part of its molecular surface; this thermodynamically unfavorable event drives oily substances out of water. Thus lipophilic substances tend to be water insoluble.

Lipopolysaccharide (LPS): Also known as lipoglycans, lipopolysaccharides are large molecules consisting of a lipid and a polysaccharide joined by a covalent bond; they are found in the outer membrane of Gram-negative bacteria, act as endotoxins and elicit strong immune responses in animals. LPS comprises three parts: the O antigen (or O polysaccharide; a repetitive glycan polymer), the core oligosaccharide, and Lipid A. The exact structure of LPS in a bacterial cell wall can be species or strain specific.

Membrane spanning peptide: A hydrophobic peptide that inserts at least partially into a lipid bilayer, or spans the length of a lipid bilayer. The membrane spanning peptide need not span the entire membrane as long as the peptide inserts to a sufficient degree for stable insertion. Exemplary proteins that include a membrane spanning peptide include CFP-10 and CEA.

Mycobactin T: (IUPAC name: [4-[(1-hydroxy-2-oxoazepan-3-yl)amino]-4-oxobutan-2-yl]6-[henicosanoyl(hydroxy)amino]-2-[[(2E)-2-(6-oxocyclohexa-2,4-dien-1-ylidene)-1,3-oxazolidine-4-carbonyl]amino]hexanoate) An iron binding compound produced by bacteria of the genus *Mycobacterium*. See, e.g., FIG. 3A and Snow, *Bacteriol Rev.* 34(2):99-125, 1970.

Pathogen Associated Molecular Pattern (PAMP): Biomarkers that are recognized by the early innate immune system in response to infection. Bacterial PAMPs are amphiphiles that possess a common structural motif that facilitates partitioning into phospholipid bilayers. These molecules can be referred to as small molecular motifs conserved within a class of microbes. They are recognized by Toll-like receptors (TLRs) and other pattern recognition receptors (PRRs) in both plants and animals, and stimulate (activate) a TLR response in cell-based assays such as those described herein.

PAMPs activate innate immune responses, protecting the host from infection, by identifying some conserved non-self molecules. Bacterial lipopolysaccharide (LPS), an endotoxin found on the bacterial cell membrane of a bacterium, is considered to be the prototypical PAMP. LPS is specifically recognized by TLR4, a recognition receptor of the innate immune system. Other PAMPs include bacterial flagellin (recognized by TLRS), lipoteichoic acid from Gram+ bacteria, peptidoglycan, and nucleic acid variants normally associated with viruses, such as double-stranded RNA (dsRNA), recognized by TLR3 or unmethylated CpG motifs, recognized by TLR9.

The term "PAMP" is somewhat of a misnomer, as most microbes, not only pathogens, express the molecules detected; the term microbe-associated molecular pattern (Ausubel, *Nature Immun.* 6(1):973-979, 2005)), or MAMP (Didielaurent et al., *Cell Mol. Life Sci.* 62(2):1285-1287, 2006), has therefore been proposed. A virulence signal capable of binding to a pathogen receptor, in combination with a MAMP, has been proposed as one way to constitute a (pathogen-specific) PAMP (Rumbo et al., *FEBS Letters* 580(12):2976-2984, 2006). Plant immunology frequently treats the terms PAMP and MAMP interchangeably, considering them to be the first step in plant immunity, PTI (PAMP-triggered immunity) (Jones & Dangl, *Nature* 444 (7117):323-329, 2006).

In various embodiments, a PAMP molecule is selected from the group consisting of flagellin, lipid A, cardiolipin, di-acyl lipopeptide, tri-acyl lipopeptide, peptidoglycan, lipoarabinomannan (LAM), phenolic glycolipid 1 (PGL-I), mycobactin T, lipopolysaccharide (LPS) and culture filtrate protein 10 (CFP-10).

PAMP Fingerprint or Profile: A distinct or identifiable pattern of PAMP levels, for instance a pattern of high and low level PAMPs in a defined set, such as a stage of a (bacterial) disease, presence or absence of (bacterial) infection, and so forth. PAMP profiles or fingerprints (also referred to as linked profiles, e.g., a disease-linked profile or disease stage-linked profile) can be linked to particular bacterial infection, to a particular stage of bacterial disease development (or infection by at least one bacterium along with co-infection by at least one other organism), normal (non-infected) subject samples (including subjects "infested" with one or more non-pathogenic bacterial species), antibiotic susceptibility or resistance, or to any other distinct or identifiable condition that influences production/release and/or levels of PAMP molecules (e.g., concentrations) in a predictable or associatable way.

PAMP profiles/fingerprints can include relative as well as absolute levels of specific PAMP molecules. The set of PAMP molecules and levels thereof in an individual sample is referred as the individual PAMP profile of that sample, which serves as a molecular signature not unlike a genomic profile or metabolomics profile—though a PAMP profile is specific for an infection or state of infection and so forth.

Figure 2:
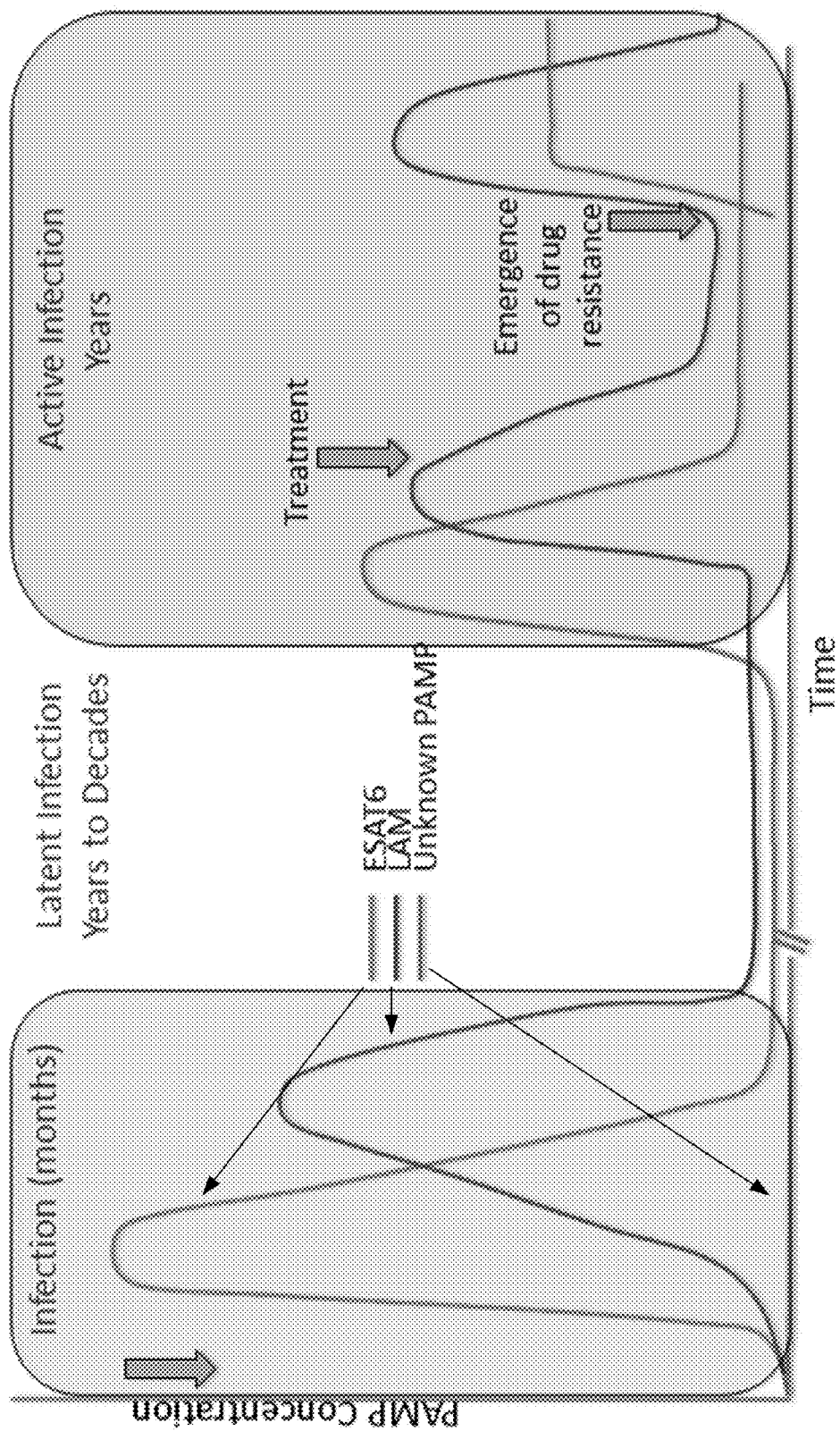
FIG. 2 is a schematic illustrating representative ways in which PAMPs can be used to track disease progression. Expression of pathogen-specific PAMPs changes during the course of a disease, and can be used to predict conversion (latent to active), response to treatment, emergence of drug resistance, relapse of infection, and so forth. Though the figure is illustrated with reference to early secretory antigen 6 (ESAT-6) and LAM, it is believed that other PAMPs (including in other diseases) will also vary such that the levels and set of PAMPs detected in a subject sample at any time (or over a course of time) can be used to track disease characteristics in that subject.

It is also contemplated that a "profile" may refer to the longitudinal change in PAMP molecule levels through time. FIG. 2, for instance, illustrates a longitudinal profile of PAMP levels as they change through time.

Peptidoglycan: Also known as murein, peptidoglycan is a polymer consisting of sugars and amino acids that forms a mesh-like layer outside the plasma membrane of bacteria, forming the cell wall. The sugar component consists of alternating residues of β-(1,4) linked N-acetylglucosamine and N-acetylmuramic acid. Attached to the N-acetylmuramic acid is a peptide chain of three to five amino acids; the peptide can be cross-linked to the peptide chain of another strand forming the 3D mesh-like (cross-linked) layer. Peptidoglycan serves a structural role in the bacterial cell wall, giving strength as well as counteracting the osmotic pressure of the cytoplasm.

Phenolic glycolipid: A class of mycoside compound produced by *Mycobacterium* and comprising an oligosaccharide moiety linked to a phenolphthiocerol molecule mainly esterified by mycoserosic acids (FIG. 3A). Phenolic glycolipids are immunogenic with their carbohydrate at the non-reducing end. PGL-I is a major antigen characteristic of *M. leprae*, forming a loose extracellular capsule around the *bacillus*. PGL-I is a suspected PAMP.

Pattern recognition receptors (PRR): A class of innate immune response-expressed proteins that respond to pathogen-associated molecular patterns (PAMP) and endogenous stress signals termed danger-associated molecular patterns (DAMP). Pattern recognition receptors (PRRs) include: Membrane-associated PRR (such as TLRs, which sense pathogen-associated or danger-associated molecular patterns extracellularly or in endosomes and receptors may link innate and adaptive immune responses); Cytoplasmic PRRs of the CATERPILLER family (also known as NACHT-leucine-rich repeat (NLR) proteins) (e.g., Nucleotide-binding oligomerization domain proteins (NODs) recognize intracellular MDP (muramyl dipeptide) and transduce signals via NF-κB and MAP kinase pathways through the serine/threonine kinase RIP2. The nucleotide-binding oligomerization domain binds nucleotide triphosphate. NODs signal via N-terminal caspase recruitment (CARD) domains to activate downstream gene induction events; Pyrin domain-containing proteins (NALPs) contain a nucleotide binding site (NBS) for nucleotide triphosphates plus C-terminal leucine-rich repeats (LRRs), which appear to act as a regulatory domain and may be involved in the recognition of microbial pathogens. NALPs appear to recognize endogenous or microbial molecules or stress responses and to form oligomers with caspase-1, which cleave IL-1 into its active form; RNA helicases—LGP2 acts as a dominant-negative inhibitor, and RIG-I and Mda5 activate antiviral signaling. These RNA Helicases recruit factors via twin N-terminal CARD domains, activate antiviral gene programs; and plant R proteins that share structural and functional similarity with PRRs found in higher animals); and Secreted PRRs (such as complement receptors, collectins; pentraxin proteins (including serum amyloid P component (SAP), acute-phase C-reactive protein (CRP), cytokine-modulated PTX3); lipid transferases; and peptidoglycan recognition proteins (PGRs), which are critical for insect immunity, and but less well characterized in mammals).

Target moiety: As used herein, any molecule or compound having a lipophilic portion of sufficient size and chemical composition whereby the at least one target moiety inserts into a lipid assembly or structure (such as a lipid monolayer, micelle, bilayer, or vesicle). Representative and non-limiting examples of target moieties are known bacterial PAMPs and putative PAMPs, including particularly the PAMP molecules discussed herein. In some embodiments, the target moiety is an amphiphile, such as a compound with an aliphatic chain that inserts into the lipid assembly. In particular examples, the amphiphile includes an acyl chain that inserts into the membrane. In other embodiments, the target moiety is a protein with a membrane spanning peptide, such as a hydrophobic peptide that spans the membrane or inserts at least partially into the membrane.

Toll-like receptor (TLR): A type I transmembrane protein characterized by an extracellular domain containing leucine-rich repeats (LRRs) and a Cytoplasmic tail that contains a conserved region called the Toll/IL-1 receptor (TIR) domain, which protein acts as a pattern recognition receptor (PRR). Toll-like receptors play a role in innate immunity, for example, by recognizing conserved microbial structures or Pathogen-Associated Molecular Patterns (PAMP). Thirteen TLRs (named TLR1 to TLR13) have been identified. However, equivalents of certain TLR found in humans are not present in all mammals. For example, a gene coding for a protein analogous to TLR10 in humans is present in mice, but appears to have been modified by a retrovirus. On the other hand, mice express TLRs 11, 12, and 13, none of which are represented in humans.

Representative nucleic acid sequences that encode human TLRs, and corresponding protein sequences are publically available, e.g., as shown in Table 4 (all GenBank numbers referred to herein are incorporated by reference for the sequence as it was publicly available on Jun. 21, 2011). Naturally occurring and artificial ligands of several TLRs have been characterized. Exemplary ligands are listed in Table 4; see also "Toll-Like Receptors (TLRs) and Innate Immunity" in *Handbook of Experimental Pharmacology*, 183:1-20, 2008. A TLR ligand is said to "activate" a TLR receptor or "stimulate" TLR pathway activity if the ligand binds to the receptor, and such binding results in the initiation of one or more signaling events, such as translocation or phosphorylation of the TLR receptor and/or other signaling molecules.

TABLE 4

Exemplary TLR sequences and ligands.

|      | GenBank nucleic acid sequences | GenBank protein sequences | Ligands | Cell types | Location |
|------|-------------------------------|---------------------------|---------|------------|----------|
| TLR1 | U88540; AB445617.1; BC141321.1 | AAC34137; AB445617; AAI41320.1 | multiple triacyl lipopeptides | monocytes/macrophages; a subset of dendritic cells; B lymphocytes | cell surface |
| TLR2 | U88878; NM_011905.3 | AAC34133.1; AAD49335.1 | multiple glycolipids, lipopeptides, and lipoproteins; lipoteichoic acid; HSP70; zymosan (beta-glucan); MALP-2; HSP70 | monocytes/macrophages; myeloid dendritic cells; mast cells | cell surface |
| TLR3 | U88879; NG_007278.1; NM_126166.4 | AAC34134.1; BAG55028.1; AAH99937.1 | poly I:C; poly(I:$C_{12}$U); dsRNA (a viral product) | dendritic cells; B lymphocytes | cell compartment |
| TLR4 | U88880; NG_011475 | AAC34135.1; CAH72619.1; CAH72618.1; AAD29272.1 | lipopolysaccharides (LPS); peptidoglycan fragments (glycopeptides); several heat shock proteins; fibrinogen; heparan sulfate fragments; hyaluronic acid fragments | monocytes/macrophages; myeloid dendritic cells; mast cells; intestinal epithelium | cell surface |
| TLR5 | AB060695.1; BC125247 | ACM69034.1; BAB43955.1; AAI25248.1; NP_058624.2 | flagellin | monocyte/macrophages; a subset of dendritic cells; intestinal epithelium | cell surface |
| TLR6 | AB020807; EU195556.1; NM_011604.3 | ABY67133.1; NP_035734.3 | multiple diacyl lipopeptides | monocytes/macrophages; mast cells; B lymphocytes | cell surface |
| TLR7 | AF245702; AK313858 | AAF78035.1; BAG36586.1; CAM14953.1 | gardiquimod; single stranded RNA (such as viral RNA); bropirimine; loxoribine; imidazoquinoline; imiquimod; resiquimod | monocytes/macrophages; plasmacytoid dendritic cells; B lymphocytes | cell compartment |
| TLR8 | AF245703; BC132054.1 | AAF78036.1; CAM14949.1 | single stranded RNA (such as viral RNA); resiquimod | monocytes/macrophages; a subset of dendritic cells; mast cells | cell compartment |
| TLR9 | AB045181.1; AF245704; AF259262; AF259263 | AAF78037.1; BAB19260.1; AAK28488.1 | CpG oligonucleotides; unmethylated CpG DNA (such as those found in the genome of bacteria and viruses) | monocytes/macrophages; plasmacytoid dendritic cells; B lymphocytes | cell compartment |

TABLE 4-continued

Exemplary TLR sequences and ligands.

| | GenBank nucleic acid sequences | GenBank protein sequences | Ligands | Cell types | Location |
|---|---|---|---|---|---|
| TLR10 | AF296673; AB445680.1; NM_001146035.1 | AAK26744.1; BAG55077.1; NP_001139507 | | monocytes/macrophages; B lymphocytes | cell surface |
| TLR11 | FJ539013.1; AY510704.1 | AAS37672.1; ACL80330.1 | Profilin | monocytes/macrophages; liver cells; kidney; bladder epithelium | cell compartment |
| TLR12 | NM_001108682.1; NM_205823.2 | NP_001102152.1; AAS37673.1 | | | |
| TLR13 | NM_205820.1 | AAS37674.1 | | | cell compartment |

It is noted that only PAMPs derived from bacteria are characterized by including an amphipathic nature that permits the compound/molecule to insert (at least partially) into a lipid assembly as described herein, and therefore be captured (and concentrated) using one of the direct or indirect (sandwich, e.g., to capture native HDL or LDL particles) lipid capture assays described herein. Thus, the TLRs that are activated by bacterial PAMPs (e.g., TLR1, TLR2, TLR4, TLR5, TLR6) are more relevant to the assays described herein, and particularly to the systems described for identifying and characterizing new PAMPs.

TLRs play a critical role in the early innate immune response to invading pathogens by sensing microorganisms. These evolutionarily conserved receptors, homologues of the *Drosophila* Toll gene, recognize highly conserved structural motifs only expressed by microbial pathogens, called pathogen-associated microbial patterns (PAMPs). PAMPs include various bacterial cell wall components such as lipopolysaccharide (LPS), peptidoglycan (PGN) and lipopeptides, as well as flagellin, bacterial DNA and viral double-stranded RNA.

Stimulation of TLRs by PAMPs initiates signaling cascades that involves a number of proteins, such as MyD88, TRIF and IRAK (Medzhitov et al., *Nature*, 388(6640):394-7, 1997). These signaling cascades lead to the activation of transcription factors, such as AP-1, NF-κB and IRFs inducing the secretion of pro-inflammatory cytokines and effector cytokines that direct the adaptive immune response.

TLRs are predominantly expressed in tissues involved in immune function, such as spleen and peripheral blood leukocytes, as well as those exposed to the external environment such as lung and the gastrointestinal tract. Their expression profiles vary among tissues and cell types. TLRs are located on the plasma membrane with the exception of TLR3, TLR7, TLR9 which are localized intracellularly (Nishiya & DeFranco et al., *J Biol Chem.* 279(18):19008-17, 2004).

Ten human and twelve murine TLRs have been characterized, TLR1 to TLR10 in humans, and TLR1 to TLR9, TLR11, TLR12 and TLR13 in mice, the homolog of TLR10 being a pseudogene. TLR2 is essential for the recognition of a variety of PAMPs from Gram-positive bacteria, including bacterial lipoproteins, lipomannans and lipoteichoic acids. TLR3 is implicated in virus-derived double-stranded RNA. TLR4 is predominantly activated by lipopolysaccharide. TLR5 detects bacterial flagellin. TLR9 is required for response to unmethylated CpG DNA. TLR7 and TLR8 recognize small synthetic antiviral molecules (Jurk et al., *Nat Immunol,* 3(6):499, 2002), and recently single-stranded RNA was reported to be their natural ligand (Heil et al., *Science.* 303(5663):1526-9, 2004). TLR11(12) has been reported to recognize uropathogenic *E. coli* (Zhang et al., *Science.* 303:1522-1526, 2004) and a profilin-like protein from *Toxoplasma gondii* (Lauw et al., *Trends Immunol.* 26(10):509-11, 2005).

The repertoire of specificities of the TLRs is apparently extended by the ability of TLRs to heterodimerize with one another. For example, dimers of TLR2 and TLR6 are required for responses to diacylated lipoproteins while TLR2 and TLR1 interact to recognize triacylated lipoproteins (Ozinsky et al., *PNAS USA,* 97(25):13766-71, 2000). Specificities of the TLRs are also influenced by various adapter and accessory molecules, such as MD-2 and CD14 that form a complex with TLR4 in response to LPS (Miyake et al., *Int Immunopharmacol.* 3(1):119-28, 2003).

Unless otherwise explained, all technical and scientific terms used herein have the same meaning as commonly understood by one of ordinary skill in the art to which this invention belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Overview of Several Embodiments

Provided herein are methods for detecting, identifying, and characterizing biomarkers, including but not limited to bacterial PAMPs. Very generally, two broad types of assay methods are provided: (1) Assays in which target moieties are captured from a sample using a lipid assembly (such as a synthetic lipid construct) that is brought into contact or exposed to the sample, allowing target moieties with certain characteristics to insert (partition) at least partially into the lipid assembly (see, e.g., FIG. 1A), then the lipid assembly/target moiety complex is harvested and further analysis can take place; and (2) Assays in which naturally occurring lipid assemblies (e.g., HDL or LDL particles, cell membranes, etc.) that are already in contact with the target moiety(s) are harvested (e.g., based on the presence of a marker in or associated with the naturally occurring lipid assembly, such as ApoA-1), with the targeting moieties already inserted/embedded therein (see, e.g., FIG. 1B), followed by further analysis. Additional specific examples are provided herein, as are methods of using biomarkers measured and/or identified using these direct and indirect lipid insertion assays.

A first embodiment provides a method of capturing at least one target moiety from a sample, which target moiety is characterized by having a lipophilic portion of sufficient size and chemical composition whereby the at least one target moiety inserts into a lipid assembly, the method comprising exposing a lipid assembly to the sample for sufficient time for one or more target moieties, if present in the sample, to insert into the lipid assembly; harvesting the lipid assembly with the one or more inserted target moiety; and separating the one or more inserted target moiety from the lipid assembly.

In some embodiments, the target moiety is an amphiphilic molecule, such as, but not limited to LAM, LPS, mycobactin T, PGL-I or lipomannan. In other embodiments, the target moiety is a protein biomarker, such as, but not limited to CFP-10 or CEA.

In various examples of this embodiment, the lipid assembly comprises a substantially planar lipid structure (for instance, a supported lipid bilayer (SLB), a tethered bilayer lipid membrane (t-BLM), a self-assembled monolayer (SAM), or a combination thereof), a vesicle (e.g., a multi-lamellar vesicle, a unilamellar vesicle, or a mixture thereof), a liposome, a nanodisc, a bicelle, or a micelle. Optionally, the substantially planar lipid structure in some instances is upon a functionalized waveguide surface.

Optionally, the lipid assembly may have inserted into it (that is, embedded into the lipid component) or otherwise associated with it (for instance, on the surface of the lipid assembly, or wrapped around a raft of lipids or lipid bilayer, and so forth) an additional compound that is not the target moiety, for instance at least one protein or peptide other than the target moiety. In examples of such a lipid assembly, the protein is a lipoprotein, for instance an apolipoprotein such as (but not limited to) Apo-A1. In methods employing a lipid assembly that contains a non-target moiety compound, harvesting the lipid assembly with the inserted target moiety will in some instances comprise immune capture of the protein or peptide other than the target moiety.

In any of these lipid insertion assays, the lipid assembly may optionally include a naturally occurring or synthetic HDL particle, a naturally occurring or synthetic LDL particle, or a mixture thereof.

Also provided are methods in which one or more target moieties separated from the lipid assembly is further characterized. Further characterizing one or more target moieties may include subjecting the compounds to at least one of mass spectroscopy (e.g., ESI MS, MALDI, MALDI-TOF, APCI), chromatography, NMR, electrophoresis, TLR activity assay, and NOD activity assay.

It is also specifically contemplated that characterizing the one or more target moieties in some cases includes identifying a set (collection, profile, fingerprint) of two or more target moieties characteristic of the sample.

Optionally, in any of the provided methods at least one of the target moieties is a bacterial pathogen associated molecular pattern (PAMP) molecule or a putative PAMP molecule. For instance, the PAMP molecule or putative PAMP molecule may be selected from the group consisting of cardiolipin, culture filtrate protein 10 (CFP-10), di-acyl lipopeptide, flagellin, lipoteichoic acid, lipid A, lipoarabinomannan (LAM), lipopolysaccharide (LPS), mycobactin T, peptidoglycan, phenolic glycolipid I (PGL-I), and tri-acyl lipopeptide. Given that the described methods enable discovery of new PAMPs (and other biomarkers), in some embodiments the target moiety is a molecule that was previously not identified as a PAMP molecule and is characterized by: having a lipophilic portion or other structural characteristics of sufficient size and chemical composition whereby the target moiety inserts into a lipid assembly; stimulating TLR pathway activity in a cell-based TLR activity assay; and being present in a sample from a subject exposed to or infected by a bacterial pathogen from which the PAMP is derived.

In some embodiments, the target moiety is a biomarker for cancer, such as carcinoembryonic antigen (CEA).

Also provided herein is method of capturing at least one target moiety from a sample, which target moiety is characterized by having a lipophilic portion of sufficient size and chemical composition whereby the at least one target moiety inserts or partitions into a lipid assembly, the method comprising: harvesting a naturally occurring lipid assembly from the sample, which lipid assembly has inserted into it the one or more inserted target moiety; and separating the one or more inserted target moiety from the lipid assembly. In some examples of this method, the naturally occurring lipid assembly comprises a HDL particle, a LDL particle, a cell membrane, or a combination of two or more thereof.

A method of capturing at least one target moiety from a sample, which target moiety is characterized by having a lipophilic portion of sufficient size and chemical composition whereby the at least one target moiety inserts into a lipid assembly, is also provided, in which the method comprises both: (1) exposing a synthetic lipid assembly to the sample for sufficient time for one or more target moieties, if present in the sample, to insert into the lipid assembly; harvesting the synthetic lipid assembly with the one or more inserted target moiety; and separating the one or more inserted target moiety from the synthetic lipid assembly; and (2) harvesting a naturally occurring lipid assembly from the sample, which lipid assembly has inserted into it the one or more inserted target moiety; and separating the one or more inserted target moiety from the lipid assembly. This method permits capture of both target moieties that are "trapped" in a native membrane in the sample along with those that are "free" to partition into a synthetic lipid assembly to which the sample is exposed.

Also provided herein is method of assessing disease state in a first subject, comprising taking a biological sample from the first subject; analyzing the biological sample using a direct or indirect lipid capture assay described herein to produce a test PAMP profile or fingerprint for the sample; comparing the test PAMP profile for the sample with a second PAMP profile, which PAMP profile is for a second sample selected from: a sample taken from the first subject at a different time point; a sample taken from a second subject; and drawing a conclusion about the disease state of the first subject based on differences or similarities between the test PAMP profile and the second PAMP profile. By way of example, drawing a conclusion about the disease state of the first subject may comprising determining that the subject is infected with a disease, has been exposed to a disease organism but is not yet infect, has a certain stage of a disease, is infected with a resistant (or susceptible) version of a disease organism, and so forth. In various examples, the disease organism is bacterial.

In specific examples methods of assessing disease state in a first subject, the second sample is a sample taken from the first subject at an earlier time point than the test sample, and the method assesses one or more of: exposure of the first subject to a bacterial organism; infection of the first subject with a bacterial organism; progression or regression of a bacterial infection of the first subject; transition of a bacterial infection of the subject from latent to active infection; response to a treatment for a bacterial infection of the first subject, which treatment was applied between the time points of the two samples; development of antibiotic resistance in an infectious bacterial organism to which the first subject has been exposed; and infection of the first subject with both a bacterial organism and a second infectious organism.

In other examples of methods of assessing disease state in a first subject, the second sample is a sample taken from a second subject, and the method assesses one or more of: exposure of the first subject and second subjects to the same or a different bacterial organism; infection of the first subject and second subject with the same or a different bacterial organism; progression or regression of a bacterial infection of the first subject and/or the second subject; transition of a bacterial infection of the first subject and/or the second from latent to active infection; response to a treatment for a bacterial infection of the subject and/or the second subject, which treatment was applied between the time points of the two samples; development of antibiotic resistance in an infectious bacterial organism; and infection of the first subject with an additional infectious agent, where the first and second subjects are infected by a bacterial organism.

Yet another method described herein is a method of detecting a biomarker in a sample, which biomarker is characterized by having a lipophilic portion of sufficient size and chemical composition whereby the biomarker inserts into a lipid bilayer of a vesicle comprising Apo-A1. Such methods involve exposing a vesicle comprising Apo-A1 to the sample for sufficient time for the biomarker, if present in the sample, to insert into the lipid bilayer of the vesicle; harvesting the vesicle with the inserted biomarker using Apo-A1 affinity capture (e.g., comprising incubating the vesicle with or expositing the vesicle to an Apo-A1 specific antibody); and examining the vesicle for the presence of the biomarker. In examples of this method, the biomarker is a PAMP or a set of PAMPs.

It is contemplated that the vesicle comprising Apo-A1 in the described methods may be either a natural HDL particle or a synthetic lipid particle, for instance a synthetic HDL particle mimic.

In examples of these methods, examining the vesicle for the presence of the biomarker comprises contacting the vesicle with an affinity molecule specific for the biomarker. One example of such an affinity molecule is an antibody specific for the biomarker. Optionally, the affinity molecule is detectably labeled.

In any of the described methods or systems, it is understood that the samples may come from a human or a non-human animal. By way of non-limit example, the non-human animal in some instances is a marmoset, a rabbit, a mouse, an armadillo, a guinea pig, or any other animal from an animal model that is useful in characterizing a bacterial infection.

IV. Lipid Assembly Insertion Assays

Lipid insertion of PAMPs and related lipid biomarkers has been exploited as a detection platform where the bilayer serves to "capture" the marker; subsequent exposure to a labeled recognition molecule (e.g., an antibody with a detectable label) can report this binding. Ultra-sensitive and specific single-reporter fluorescence based assays for bacterial lipopolysaccharide (LPS) and mycobacterial lipoarabinomannan (LAM) have been developed using this platform; see, e.g., Published patent application US 2011/0008798, which is incorporated herein in its entirety. Other PAMPs including CFP-10 have now also been captured and assayed using this lipid bilayer insertion assay. Additional amphiphilic compounds including putative PAMPs such as peptidoglycans (e.g., PGL-I) and mycobactin T have also been captured using lipid assembly assays. This system can be applied to all lipophilic targets in order to achieve sensitive detection.

Lipid Capture Assemblies

Provided herein are methods of insertional capture that employ different types of lipid capture assemblies, including synthetic (manufactured) assemblies and naturally-occurring lipid structures (e.g., lipid-containing structures that are extracted from a subject or living cell or system).

In some embodiments, the lipid capture assembly comprises an artificial or synthetic lipid structure such as a synthetic lipid bilayer or self-assembly monolayer or synthetic micelles, bicelles, vesicles, liposomes, and so forth. In such embodiments, the lipid assembly is brought into contact with the target moiety(s) (or a sample that contains or is suspected of containing such moiety(s)) for a period of time sufficient for at least some of the target to partition into the lipid assembly. Various specific examples of this technology are described herein, including for instance insertional assays to detect LAM, LPS, PGL-1, and mycobactin T.

The lipid components that can be used for forming the synthetic lipid bilayers in the presently described technology are generally described in the literature. Generally, these components are phospholipids (e.g., egg phosphatidylcholine, dipalmitoylphosphatidylcholine and distearoylphosphatidylcholine), such as, for example, phosphatidylcholines, phosphatidylethanolamines, phosphatidylglycerols, phosphatidylserines, phosphatidic acids, phosphatidylinositols sphingolipids, cerebrosides, gangliosides, and combinations of two or more thereof. They may have lipid portions of varying length or may be of the same length. Optionally, the lipid bilayers also comprise one or more steroids, such as cholesterol.

Formation of a synthetic lipid bilayer upon a surface, e.g., a waveguide surface, can be accomplished by vesicle fusion, a process well known to those skilled in the art. Specific embodiments employ lipid capture assemblies that are substantially planar synthetic lipid monolayers or bilayers, for instance supported lipid bilayers formed on a solid surface such as a waveguide or the like (see, e.g., devices and methods described in U.S. Pat. No. 7,190,851). See also Martinez et al., *J. Mater. Chem.* 15, 4639-4647, 2005.

In other embodiments, the lipid capture assemble comprises a naturally occurring lipid particle or structure, such as HDL, LDL, a cell membrane, or so forth. In such instances, the natural lipid assembly is in contact with and will usually have already absorbed the target moiety without intervention. In examples of these methods, the natural lipid structure (containing known or suspected target moieties) is isolated or otherwise removed from its natural environment so that the partitioned target moieties can be identified, detected, and/or measured. By way of example, this embodiment is described herein in the context of detecting LAM in HDL from blood/serum, using a sandwich assay in which the primary capture antibody is anti-Apo-A1.

Target Moieties

The observation that lipophilic (or amphipathic) pathogen associated molecular patterns (PAMPs) insert at least partially into a lipid bilayer or other lipid assembly has been exploited to develop sensor platforms for the ultra-sensitive and specific detection of PAMPs, such as those associated with bacterial disease. This technology has been validated with lipoarabinomannan (LAM) from *Mycobacterium tuberculosis* and lipopolysaccharide (LPS), associated with gram-negative bacteria, as well as CFP-10 and lipomannan from *M. bovis*. This technology has also been used to pull down putative PAMPs, such as PGL-I and mycobactin T, as well as other important biomolecules, such as CEA (a breast cancer biomarker). This platform is believed to be applicable to all lipophilic target molecules and target molecules with a membrane spanning peptide (and more broadly, to all targets that are able to partition at least partially into a lipid assembly, including molecules that undergo a confirmation rearrangement in order to insert into a lipid environment) associated with pathogens (and other disease biomarkers) and thus, is the basis of a very simple and specific sensing platform. In some embodiments, the target moiety that partitions at least partially into a lipid assembly is an amphiphilic molecule, such as LAM, LPS, lipomannan, PGL-I or mycobactin T. In other embodiments, the target moiety is a protein with a membrane spanning domain (referred to herein as a "protein biomarker"), such as CFP-10 or CEA.

Use of (Direct or Indirect) Lipid Assembly Insertion Assays to Develop Expression Profiles The assays described herein enable identification of biomarker expression profiles or patterns (e.g., molecular fingerprints) that are linked to various the state or condition of the subject from which the sample was taken. By way of example, it is contemplated that biomarker profiles can be identified that are signatures for different stages of disease or infection (such as infection with a bacterium) (see, e.g., FIG. 2); transitions in disease progression (such as latent to active, susceptible to resistant); co-infection of the subject by multiple organisms (such as two infectious bacteria, each of which contributes molecule(s) to the profile; or one infectious bacterium coupled with one or more other infectious organisms that alter the biomarker profile of the infectious bacterium); exposure to a disease organism without active infection; the presence of mixtures of non-infectious (benign) bacteria in the subject (e.g., healthy background profiles) and so forth.

Identified profiles/fingerprints can be used for various purposes, including but not limited to: disease tracking and surveillance, diagnosis, assessment of treatment, and so forth.

Use of Lipid Assembly Insertion Assay for Disease Surveillance

The outbreak of a new and rapidly progressing infectious disease can, if left unchecked, elicit very high morbidity and mortality. As discussed in the 2007 World Health Organization report (World Health Organization, Report for Early Detection and Diagnosis. "A safer future: global public health security in the 21st century". http://www.who.int/whr/2007/overview/en/index.html), early detection and diagnosis followed by effective response, can significantly reduce the number of infections. Severe acute respiratory syndrome, SARS, a virus that first appeared in 2003, nearly caused a pandemic (Heyman & Rodier, "Global surveillance, National Surveillance and SARS", (2004), Emerging Infectious Diseases, available on the World Wide Web at .medscape.com/viewarticle/467371). Within a matter of weeks the infection had spread from one province in China to 37 countries, eventually infecting 8,422 and causing 916 deaths. SARS has been fully contained, largely as a result of an aggressive effort by the World Health Organization and others, to put in place effective detection, diagnosis, and response. The goal of a global disease surveillance effort is to rapidly detect and diagnose infection to help guide public health decisions aimed at controlling the spread of infection.

In contrast to SARS, TB is an ancient slow growing chronic disease that is estimated to have infected ⅓rd of the world's population. Most individuals carry the bacterium as a latent infection, and will never develop active disease. Only 10% of those exposed will develop active TB in their lifetime (Dye & Williams, *Science,* 328(5980), 856-861, 2010). M. tb was perceived to be largely contained in the developed world, but this is rapidly changing with the emergence of drug resistant strains and co-infection with HIV. Both multi-drug resistant (MDR) and untreatable extensively drug-resistant (XDR) TB have been identified worldwide. Drug resistance has emerged in several other infectious diseases (e.g., methicillin-resistant *S. aureus*). Recently the New Delhi Metallolactamase-1 gene, which readily inserts into many bacteria and provides antibiotic resistance (Kumarasamy et al., *Lancet Infectious Disease,* 10(9), 597-602, 2010), has been found in drinking water in India.

M/XDR-TB strains are capable of direct transmission from person to person, increasing potential global exposure to an alarming level. The strain F15/LAM4/KZN, responsible for a highly fatal XDR-TB outbreak in Natal, S. Africa in 2004, has spread through the country in 6 years, a situation that could have been averted by effective surveillance. The overall picture is further complicated by the recent discovery of mixed-infections (Stavrum, et al., *J. Clin. Microbiol.,* 47(6), 1848-1856, 2009; Huang et al., *J. Clin. Microbiol,* 48(12), 4474-4480, 2010), substantiated by preliminary data from our team, which may be as high as 54% in some populations (Stavrum, et al., *J. Clin. Microbiol.,* 47(6), 1848-1856, 2009). Current diagnosis of resistance requires culturing of patient sputum to enrich for DNA. In the case of mixed infections, culture-based techniques can result in loss or misinterpretation of critical information, resulting in incorrect diagnosis and treatment.

Mixed infection can result from mutations in host, driven by drug pressure to create a new drug resistant strain (acquisition). Alternately, mixed infection can be a consequence of sequential exposure of the same individual to multiple strains of M. tb, some of which may be drug resistant (super-infection). Understanding the role of super-infection in the context of HIV co-infection is critical to effective surveillance: such infections may be enhanced in immunocompromised individuals with HIV, and this may explain the rapid expansion of XDR-TB in populations with high HIV prevalence. Rapid depletion of IL-2 producing TB-specific CD4 T cells during HIV-1 infection can aggravate TB10, and such individuals with compromised ability to resist M. tb may be more susceptible to super-infection with drug resistant strains (Gandhi et al., *Lancet,* 368(9547), 1575-1580, 2006).

With the provision herein of methods and systems for identifying and determining expression profiles (such as PAMP expression profiles), disease surveillance methods are now enabled. Embodiments of these methods are described in the context of global surveillance of tuberculosis (that is, *Mycobacterium tuberculosis*), including for instance drug resistant tuberculosis, but it will be apparent that these methods can be used for the surveillance of other bacterial infectious diseases (such as, but not limited to, *E. coli, Staphylococcus, Streptococcus, Vibrio cholerae, Yersinia pestis, Mycobacterium leprae, Salmonella typhimurium, Campylobacter jejuni, Helicobacter pylori, Haemophilus influenza, Klebsiella pneumonia, Legionella* sps, *Pseudomonas* sps, any gram negative bacteria having Lipopolysaccharide, any gram positive bacteria having lipoteichoic acid) as well as the surveillance of other changes in infectious disease (e.g., altered virulence, association with co-infective agents, and so forth) and changes in expression or expression levels of PAMPs due to various reasons. Thus, the provided methods are not limited to monitoring tuberculosis or monitoring development or spread of antibiotic resistance.

A comprehensive system of global surveillance for drug resistant TB involves 1) sample collection at numerous sites with minimal infrastructure, 2) onsite preliminary determination of active infection, and 3) deactivation and transport of biological samples (e.g., urine, serum and sputum) to a high throughput facility to screen for drug resistance. However, current technology to diagnose active infection and screen for drug resistance are inadequate. Moreover, the sample numbers for a disease as prevalent as TB are high (350,000/yr in South Africa) (Global TB Control Report, 2010, WHO, ISBN 978924 1564069), requiring a high-throughput laboratory network (HTLN). The technology described herein enables a HTLN for surveillance of drug resistant TB (and other bacterial infections).

M. tb can survive in the infected host for decades without causing disease (latent TB). A change in one of many variables can result in disease manifestation (active TB). By providing an "active-specific" or "latent-to-active specific" PAMP molecule profile using the described lipid assembly insertion assays, resources can be focused on the diagnosis of active infection. Diagnosis of infection will be based on quantitative detection of PAMP profiles such as those described herein. First, the lipid assembly insertion assay system is used to isolate and identify PAMPs from infected patients and animals, and study specific PAMP molecule and PAMP expression profile as a function of disease progression.

The methods described herein can also be used to characterize complex infections where a single individual harbors multiple infectious organisms, for instance multiple M. tb strains, which may have distinct drug resistance profiles (mixed infections). The etiology of such infections is not understood, nor is their impact on diagnosis and surveillance of TB. The lipid assembly insertion assay will be used to characterize mixed infections, and methods to reliably detect and screen for drug resistance in such complex samples developed based on the characteristic PAMP profiles identified. A longitudinal study in humans and animals can be carried out, to determine PAMP presence and concentrations (and optionally M. tb gene expression). Such studies are useful to identify biomarkers for diagnosis of active (opposed to latent) TB infection; and inform on changes in PAMPs with emergence of drug resistance.

Detection of PAMPs in Infected Patients

Lipoarabinomannan (LAM), a cell-wall component of M. tb, and other PAMPs have been detected in patients. Circulating concentrations of PAMPs vary depending on the biological sample and state of disease. Two of the recent developments in TB diagnostics are based on PAMPs, namely ESAT-6 (Pai et al., *Lancet, Infectious Diseases,* 4(12) 761-76, 20) and LAM (Shah et al., *J. Acquir. Immune. Defic. Syndrome,* 52(2), 145, 2009). Detection of LAM in urine is the basis of the Inverness® assay for TB, but the assay lacks adequate sensitivity to eliminate false-negatives. Our sandwich assay for LAM has a much better limit of detection (1 pM), and we have used this to detect LAM in urine from patients with active infection (range, 10-150 pM). Minimizing non-specific interactions in complex biological samples (Anderson et al., *Langmuir,* 24(5), 2240-2247, 2008) helps us enhance the sensitivity of detection using our platform. However, sandwich immunoassays cannot be applied to the detection of small amphiphilic biomarkers (e.g. phenolic glycolipids and mycobactin), a limitation addressed by our membrane insertion assay (below). We believe that quantitative measurement of PAMP concentrations will permit accurate diagnosis of active TB, with low false negatives.

Exploiting the common chemistry of PAMPs for their isolation and detection: PAMPs partition into supported lipid bilayers and endogenous HDL particles (Levine et al., *Proc. Natl. Acad. Sci*., (U.S.A.), 90(24), 12040-12044, 1993; Cavaillon et al., *Infect. Immun.,* 58(7), 2375-2382, 1990). This has been previously demonstrated for *E. coli* lipopolysaccharide (Levine et al., *Proc. Natl. Acad. Sci*., (U.S.A.), 90(24), 12040-12044, 1993; Cavaillon et al., *Infect. Immun.,* 58(7), 2375-2382, 1990) and LAM (Patent application publication US 2011/0008798, which is incorporated herein by reference in its entirety).

Accordingly, two approaches for the capture and detection of amphiphilic PAMPs are described herein: membrane insertion (direct) and HDL capture using an antibody that binds apolipoprotein A1, a coat protein of HDL (indirect). The ultra-sensitive (<10 femtomolar), specific and rapid (15-30 min) detection of LAM partitioned into a bilayer (membrane insertion). The provided methods enable detection of picomolar concentrations of LAM in patient serum. Membrane insertion assays are also useful for sensitive detection of several additional amphiphiles in broad classes: *E. coli* lipopolysaccharide, phenolic glycolipids from *Mycobacterium leprae*, culture-filtrate protein-10 (CFP-10), lipomannan, LAM and mycobactin from M. tb.

The natural association of LAM with HDL has also been exploited to pull it down from serum using an antibody to apolipoprotein A1 to capture HDL on sensing films such as on waveguide transducers. This method can be used to separate PAMPs (both known and putative) from complex serum from infected and control animals and humans.

Correlating PAMP Expression to Drug Resistance

Single nucleotide polymorphisms (SNPs) in 21 strains of M/XDR-TB have been compared to 22 strains of DS-TB. Genes encoding for PAMPs or their precursors were consistently associated with greater mutations than the rest of the genome (22% vs. 10% of genes, respectively). Das et al. performed a systematic analysis of SNPs in MDR and XDR strains vs. DS ones (*J. Biosci.,* 34(3), 397-404, 2009). Two of nine SNP clusters associated with drug resistance were expressed in PAMP encoding genes. Other studies as well have reported connection of PAMP encoding genes (e.g., acyltransferases) to drug resistance (Wilson et al., *Proc. Natl. Acad. Sci*. (*U.S.A.*), 96(22), 12833-12838, 1999; Ramaswamy et al., *Antimicrob. Agents Chemother.,* 47(4), 1241-1250, 2003; Goffin & Ghuysen, *Microbiol. Mol. Biol. Rev.,* 66(4), 702-738, 2002). Based on these findings, it is believed that changes in PAMP profiles will distinguish DS from M/XDR infections.

Isolation, Characterization, and Detection of PAMPs in Serum Samples

Described herein is the first completely general approach to the in vivo study of bacterial PAMPs generated during infection. In order to develop this approach, PAMPs (and putative PAMPs) expressed during an infection are isolated using membrane insertion methods described herein and characterized both as to chemical makeup and structure as well as the ability of the putative PAMP to trigger signaling through a TLR.

Using PAMP Profiles in Disease Diagnosis

The PAMP profiles and lipid insertion assay methods described herein are excellent molecular tools to characterize and track the concentrations of PAMPs as a function of disease. PAMP profiles can be used detect active TB (in contrast to latent infection or non-infected exposure, for instance), determine bacterial load and discriminate between DS and resistant infections. The tools described herein in the context of tuberculosis can be transitioned to use with any bacterial infection, which enables new approaches to early diagnosis of infection as well as disease monitoring and surveillance.

The accurate diagnosis of infection, assessment of disease progression and screening for drug resistance are often difficult for bacterial infections. Diagnosis of active TB infection is especially difficult in countries where the disease is endemic and where the skin test cannot be used owing to universal vaccination. In these countries, sputum smear microscopy is used as a first screen of infection. Given the extremely high rates of false negatives, this test cannot be used for surveillance or to guide intervention and diagnosis for treatment is usually based on clinical suspicion rather than factual data. The PAMP discovery and phenotypic diagnostic tools described here open the door to entirely new approaches for diagnosis of active TB (and other disease) infection, as well as screening for drug resistance. The assays described herein also address issues associated with mixed infection and culture bias that affect drug resistant bacterial infections broadly. These methods also facilitate novel strategies for understanding host-pathogen interactions, particularly regarding PAMPs and the innate immune response. Understanding the mechanism of initial pathogen recognition by the host is useful for the development of novel vaccination and therapeutic strategies.

Methods of Analyzing TLR Stimulation by Putative PAMPs

Additional PAMPs (or other agonists that specifically bind to and activate a particular TLR) can be identified using cell-based assays for stimulation of TLR activity. By way of example, a reporter system can be used in which binding and activation of a selected TLR (e.g., TLR1, TLR2, TLR4, or another TLR recognized as interacting with a bacterial PAMP molecule) and induction of NF-κB is detected using an NF-κB responsive reporter construct. Cell lines, such as HEK293, stably transfected with the components necessary for signaling via a selected TLR are transfected with an NF-κB inducible reporter plasmid, pNiFty2-SEAP (InvivoGen, San Diego). This plasmid contains an engineered promoter that combines five NF-κB sites with the proximal ELAM (endothelial cell-leukocyte adhesion molecule) promoter upstream of a reporter gene encoding secreted alkaline phosphatase (SEAP). SEAP is extremely heat stable and can be detected spectrophotometrically, either colorimetrically or by detecting a luminescent product, e.g., using a PHOSPHA-LIGHT™ chemiluminescence kit (Applied Biosystems, BP3000). In this assay, the substrate CSPD [3-(4-methoxyspiro[1,2-dioxetane-3,2'(5'-chloro)-tricyclo (3.3.1.13,7)decane]-4-yl)phenyl phosphate] is dephosphorylated by SEAP, and the resulting unstable dioxetane anion decomposes and emits light at a wavelength of 477 nm. The light signal is quantified (for example using a microplate luminometer) and is linear up to five orders of magnitude and proportional to the concentration of SEAP. The extent of TLR activation can be quantified by collecting supernatant and determining the concentration of SEAP via this assay.

Cell lines expressing mouse and human TLRs 1-10 are commercially available (e.g., from InvivoGen) or can be produced by those of skill in the art using routine molecular biology procedures using publicly available TLR sequences, for example as described in Sambrook et al. (Molecular Cloning: a Laboratory Manual, Cold Spring Harbor Press, 1989).

In brief, the transfected cell line expressing the selected TLR and the parental HEK293 cells each carrying the NF-κB reporter construct are stimulated (for between 12 and 24 hours, e.g., for approximately 18 hours or overnight) with varying doses of a test agent (for instance, a putative or potential PAMP isolated through a direct or indirect lipid insertion assay described herein). Typically, each test agent is tested at multiple doses to determine a dose/response curve. Following the incubation, supernatant is collected and NF-κB activity is measured using an alkaline phosphatase assay, for instance.

PAMP Discovery and Determination of Function

This section provides an overview of how PAMPs and other amphiphilic biomarkers will be isolated from M. tb infected animals (as a model system) and humans and characterized using mass spectrometry. PAMPs will be distinguished from other amphiphilic biomarkers through cell studies, which are used to determine the putative PAMP's ability to trigger the innate immune system. The mechanism by which PAMPs initiate immune signaling can optionally be analyzed, and the results used to determine optimal sets of PAMPs for use in diagnosis, for instance as PAMP profiles.

Provided herein is a systematic discovery platform for PAMPs and other amphiphiles from infected human and animal serum, using mass spectrometry and biomarker identification. This is the first comprehensive effort to pull down PAMPs from infected animals, rather than bacterial culture. Immunoadsorption of HDL complexes, 20 nm assemblies of phospholipid bilayers stabilized by apolipoprotein-A1, will be used to capture PAMPs; it has been determined that they sequester excess inflammatory mediators in the bloodstream. HDL particles have been isolated with associated LAM and lipopolysaccharide from serum using anti-apolipoprotein antibodies. This adsorption strategy can be used to isolate novel PAMPs, for instance from the serum of infected rabbits, as a surrogate for human infection. Multiple PAMPs (including known PAMPs such as LAM) are expected to be present in the native HDL complexes. These precipitated complexes will be subjected to sequential biochemical fractionation, yielding component classes (e.g., proteins, lipids, sugars). Each of these molecular classes is then separated for instance using solid phase extraction chromatography into individual fractions that are tested for PAMP function.

A cell-based assay is used for activation of immune receptors that mediate host innate immunity in response to bacterial infection, such as toll-like receptors (TLR2 and TLR4), which recognize extracellular PAMPs, and NOD-like receptors (NOD1 and NOD2), which recognize intracellular PAMPs. Both TLRs and NOD2 signaling pathways are activated in response to M. tb infection (Ferwerda et al., *PLoS Pathog.*, 1(3), 279-285, 2005). In fact, mycobacteria express an unusually modified N-glycosylated form of muramyl peptide in its peptidoglycan, which is a more potent stimulator of NOD2 signaling than the more common N-acetyl modification (Coulombe et al., *J. Exp. Med.*, 206

(8), 1706-1716, 2009), suggesting that unique PAMPs may be isolated from M. tb using the provided discovery platform.

Human embryonic kidney reporter cell lines can be used that link activation of the TLR and NOD receptors to expression of a reporter gene, such as an enzymatic alkaline phosphatase gene. The TLR reporter cell lines are stimulated with different chromatographic fractions in order to identify HDL components that induce alkaline phosphatase (or other reporter) activity. Positive fractions will be analyzed further, for instance by MS, to identify and characterize novel PAMPs. In an iterative process, the TLR/NOD cell-based assays, and separation-MS will be used for identification of both known PAMPs (e.g., LAM), and discovery of new PAMPs.

Using these methods, a comprehensive lexicon of stimulatory PAMPs in TB infection (or another infection) is generated; this lexicon can be used to define signatures for detection of active disease, for instance. The novel PAMP compounds are validated as derived molecules from M. tb rather than the host serum by comparison to non-infected samples. In addition, PAMPs will be purified from M. tb only cultures and examined for overlap with putative PAMPs identified from infected rabbits. Optionally, biochemical strategies such as serum protein depletion can be employed to reduce complexity and enrich target molecules.

Assay Development and Longitudinal Studies of M. Tb Infection

Detection and quantification assays for the PAMPs and PAMP profiles discovered using methods described herein can be developed based on renewable recombinant antibodies from phage and yeast display, for instance. PAMP concentrations will be determined from infected patients as a function of disease progression and evolution of drug resistance. The expression levels of genes encoding PAMPs will be determined using pathogen DNA from the same patients. The expression profiles so obtained will be correlated with disease status and PAMP concentration data, to determine the PAMPs that inform on disease diagnosis and drug resistance.

The waveguide-based optical biosensor can be used for the quantitative measurement of PAMP concentrations in both animal models and human samples. Established methods for functionalization of waveguides (Levine et al., *Proc. Natl. Acad. Sci., USA,* 90(24), 12040-12044, 1993; Mukundan et al., *Bioconjug. Chem.,* 20(2), 222-230, 2009) are employed, for instance with either supported lipid bilayers or self-assembled monolayer chemistries. Sensitive detection of PAMPs will be made using lipid assembly (e.g., lipid bilayer) insertion technology. Alternative transduction schemes (e.g., sandwich immunoassays, competition assays) (Mukundan et al., *Sensors,* 9(7), 5783-5809, 2009) can also be employed.

Affinity ligands (e.g., antibodies) and assays specifically adapted to PAMP presentation in membranes can be used to determine profiles of PAMPs as a function of disease progression in both infected animals and humans. PAMP detection (such as LAM detecting) will provide accurate diagnosis of active infection with minimum false negatives and inform on bacterial load. It is also expected that drug sensitive infection can be distinguished from drug resistant infection using these methods.

For detection of PAMPs for which it is impractical or impossible to raise antibodies using phage display, commercially available affinity ligands or antibodies raised using conventional strategies (e.g., hybridomas) can be used. Sample concentration approaches may be used for those PAMPs the concentration of which may be too low to readily detect. By way of non-limit example, the described lipid assembly insertion assay can be used to concentrate PAMPs in order to accumulate sufficient for quantification or further analysis.

TB Surveillance

A rabbit model of TB infection will be used for the initial PAMP discovery wherein animals will be infected with DS-M. tb (Beijing strain). Samples (urine, serum) are collected at various times, starting before infection and culminating with animal death. Once initial discovery is accomplished, PAMP expression is evaluated in a small cohort of marmoset monkeys. Marmosets are excellent models of disease, because they occur as twins or triplets, providing a genetically identical clone as a control for infection. However, because of the small volume of samples obtained and the costs associated with the study, they will be used for confirmation of the results only.

Human samples will be obtained. Serum, urine, and sputum-derived DNA will be collected at various time points, starting at enrollment. A detailed natural history protocol will follow, with appropriate testing using conventional methods, to benchmark the disease status of enrolled patients. Many patients present with relapse, associated with drug-resistant strains, and hence, some of the samples collected will be representative of evolution of resistance and possibly, mixed infection. Once the approach is developed, the new findings will be tested using blinded archived samples from 50 MDR, XDR, and DS subjects.

The following examples are provided to illustrate certain particular features and/or embodiments. These examples should not be construed to limit the invention to the particular features or embodiments described.

EXAMPLES

Example 1: Lipid Insertion Assays

This example provides representative methods for carrying out a lipid insertion assay to detect and quantify amphipathic compounds such as PAMPs. Specific fluorescent signals are observed using, for instance, a waveguide based optical biosensor when the biomarker of interest partitions into the lipid bilayer present on the waveguide surface. In these representative embodiments, the amphipathic biomarkers are detected using a fluorescently labeled antibody specific for that biomarker.

Bilayer Preparation and Flow Cell Assembly

Silicon oxynitride (SiONx) planar optical waveguides were fabricated at nGimat (Atlanta) and have been effectively used with the waveguide-based biosensor platform for over a decade (Mukundan et al., *Sensors* 9:5783-5809, 2009). SiONx films have a thickness of ~120 nm (±5 nm) and a refractive index of 1.80±0.06. A thin ~10 nm coating of $SiO_2$ is deposited on the active waveguide surface for functionalization with a lipid bilayer.

Biotinylated (0.1%) unilamellar vesicles (bilayers) of DOPC were prepared, according to the procedure described by Martinez et al. (*J. Mater. Chem.* 15, 4639-4647, 2005).

For evaluation of the partitioning of amphiphilic antigens like LAM, PGL-I, LPS and mycobactin, waveguide surfaces were cleaned and functionalized with DOPC bilayers and then allowed to stabilize overnight (Mukundan et al., *Biocon Chem.* 2009, 20, 222-230).

To minimize non-specific binding, the bilayers were blocked for 1 hour with PBS containing 2% bovine serum albumin. After blocking, the waveguides were washed PBS containing 0.5% bovine serum albumin and then mounted in a flow cell and mounted on the optical biosensor platform.

The laser light was in-coupled through the integrated grating and the waveguide-background was measured as a baseline metric before each experiment.

Materials:

Reporter antibody for specific biomarker (LAM/PGL-I/LPS/mycobactin/lipomannan) is labeled with either Alexa-Fluor 647 or Alexa-Fluor 532 using a kit from Molecular Probes (Invitrogen, Eugene, Oreg.). Polyclonal anti-LAM antibody (used for detection of LAM and lipomannan) and polyclonal anti-PGL-I antibody were both from BEI Resources, Manassas, Va.; monoclonal anti-LPS antibody was from Abcam, Cambridge, Mass.; minibody (developed from a single chain antibody (scFv)) directed to mycobactin T was obtained from Dr. Tobin J. Dickerson, Department of Chemistry & Worm Institute of Research and Medicine (WIRM), The Scripps Research Institute, La Jolla, Calif. 92037. Standards for the biomarkers were obtained from Tuberculosis Material consortium (Colorado State University/BEI Resources, Manassas, Va.).

The following experiments were done on a waveguide based optical biosensor developed at Los Alamos National Lab. Experimental details for using this device are essentially as described in Martinez et al. (*J Mat Chem.* 15, 4639-4647, 2005), Mukundan et al. (*Bioconjugate Chem.* 20, 222-230, 2009) and Anderson et al. (*Langmuir,* 24, 2240-2247, 2008). For insertion assays generally, non-specific interactions were determined by the addition of control bovine serum (for instance, 1:10 dilution, 15 min, RT), followed by the reporter antibody. Specific detection of target moiety was then measured by the addition of the appropriate antigen (e.g., pure compound spiked into bovine serum) to the flow cell (for instance, 15 min, RT), followed by addition of the reporter antibody (for instance, 100 nM, 5 min, RT). The fluorescence signal associated with the binding of the reporter to the antigen was measured using the spectrometer of the biosensor platform.

In all experiments, the waveguide-associated background (intrinsic measure of impurities associated with the instrument itself) and coupling efficiency (typically 40-50%, incident power is 440 µW) were measured. After each addition, the flow cell was washed with PBS (~1.5 ml, 60× flow cell volume), unless otherwise specified.

LAM Assay:

For non-specific binding, fluorescently labeled reporter antibody (polyclonal LAM antibody; ~50-100 nM) was added into the flow cell and incubated for 15 minutes. The flow cell was then rinsed with ~2 ml of PBS. The background (non-specific) spectrum was collected and recorded.

Standard LAM (at different concentrations, diluted in PBS or bovine/human serum) or tuberculosis patient samples were added into the flow cell and incubated for 1 hour. Then the flow cell was rinsed with ~2 ml of PBS.

For specific binding, fluorescently labeled reporter antibody (polyclonal LAM antibody; ~50-100 nM) was added into the flow cell and incubated for 15 minutes. The flow cell was then rinsed with ~2 ml of PBS. Spectrum was collected and recorded.

Figure 1B:
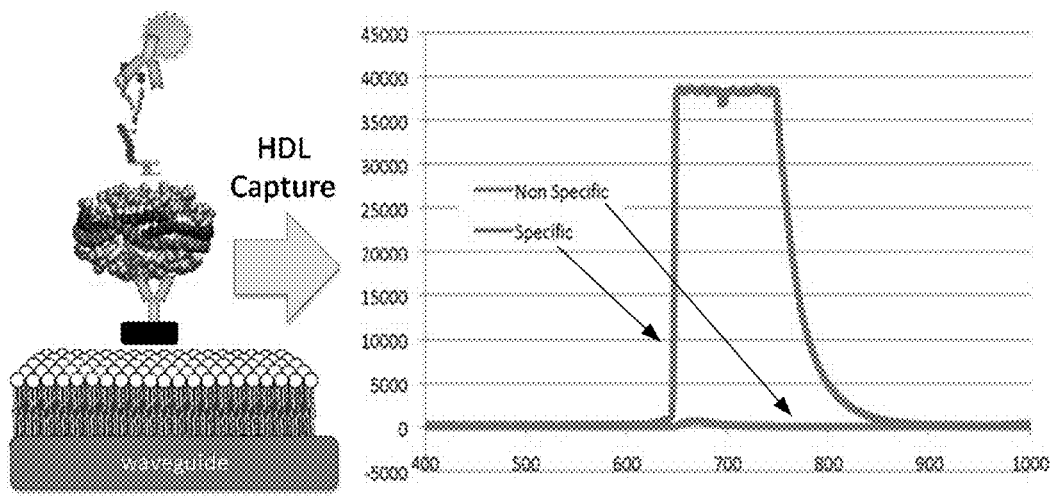
FIG. 1B is a schematic depiction of Apolipoprotein A1 capture (left panel) and detection of LAM partitioned into high density lipoprotein (HDL; right).
Figure 4:
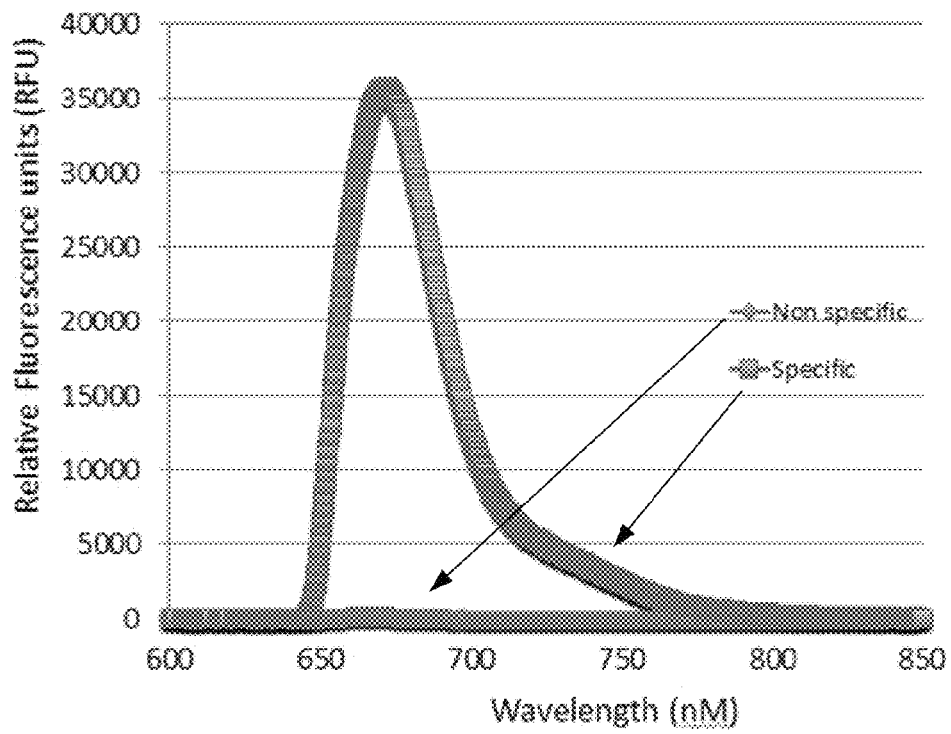
FIG. 4 is a graph illustrating detection of LAM in bovine serum by insertion assay using fluorescent-labeled anti-LAM antibody as a reporter. A known concentration of LAM (100 pM) was spiked into bovine serum, the LAM captured from the spiked serum using one embodiment of the provided lipid insertion assay (a synthetic lipid bilayer on a functionalized waveguide platform), and the amount captured measured using a fluorescent-labeled anti-LAM antibody. Non-specific (background) fluorescence is also shown.

Results:

A specific fluorescence signal (FIG. 4) was observed when LAM partitions into the lipid bilayer (supported on the waveguide surface) and is then detected using a fluorescently labeled polyclonal LAM reporter antibody. The results obtained from a similar experiment for detection of LAM is shown in FIG. 1A. The limit of detection for LAM in serum is 10 fM.

Phenolic Glycolipid (PGL-I) Assay:

For non-specific binding, fluorescently labeled reporter antibody (polyclonal anti-PGL-I antibody; ~50-100 nM) was added into the flow cell and incubated for 10 minutes. The flow cell was then rinsed with ~2 ml of PBS. The background (non-specific) spectrum was collected and recorded.

Standard PGL-I (at different concentrations, diluted in PBS or bovine/human serum) was added into the flow cell and was incubated for 1 hour. The flow cell was then rinsed with ~2 ml of PBS.

For specific binding, fluorescently labeled reporter antibody (polyclonal anti-PGL-I antibody; ~50-100 nM) was added into the flow cell and incubated for 10 minutes. The flow cell was then rinsed with ~2 ml of PBS. Spectrum was collected and recorded.

Figure 5:
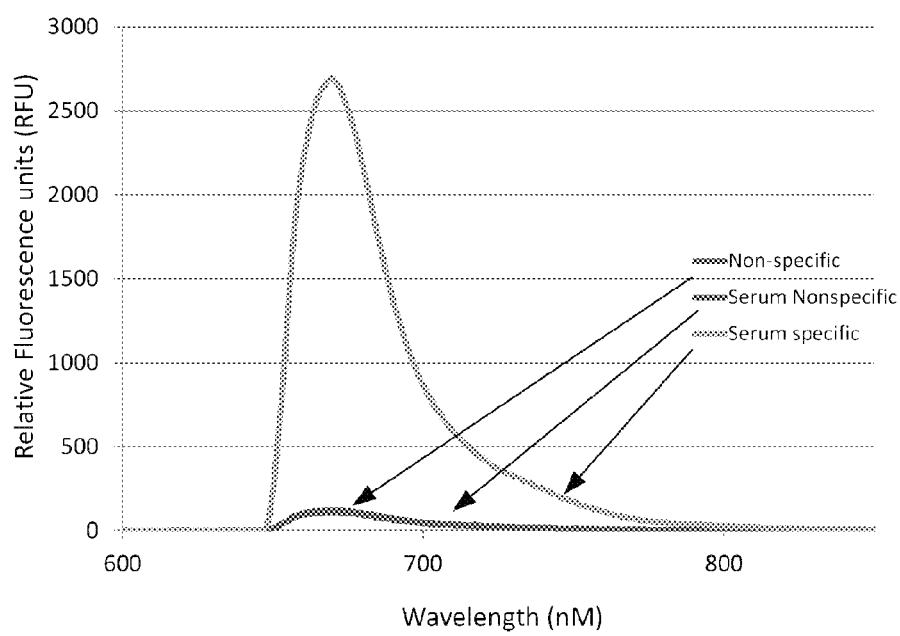
FIG. 5 is a graph illustrating detection of PGL-I in bovine serum by insertion assay using fluorescent-labeled anti-PGL-I antibody as a reporter. A known concentration of PGL-I (6.7 µM) was spiked into bovine serum, the PGL-I captured from the spiked serum using one embodiment of the provided lipid insertion assay (a synthetic lipid bilayer on a functionalized waveguide platform), and the amount captured measured using a fluorescent-labeled anti-PGL-I antibody. Non-specific (background) fluorescence is also shown.

Results:

A specific fluorescence signal (FIG. 5) was observed when PGL-I partitions into the lipid bilayer (supported on the waveguide surface) and is then detected using a fluorescently labeled polyclonal PGL-I reporter antibody.

Mycobactin T Assay:

For non-specific binding; fluorescently labeled reporter antibody (anti-mycobactin minibody; ~50-100 nM) was added into the flow cell and incubated for 30 minutes. The flow cell was then rinsed with ~2 ml of PBS. The background (non-specific) spectrum was collected and recorded.

Standard mycobactin T (at different concentrations, diluted in PBS or bovine/human serum) was added into the flow cell and was incubated for 1.50 hours. The flow cell was then rinsed with ~2 ml of PBS.

For specific binding, fluorescently labeled reporter antibody (polyclonal anti-mycobactin antibody (~50-100 nM); was added into the flow cell and incubated for 30 minutes. The flow cell was then rinsed with ~2 ml of PBS. Spectrum was collected and recorded.

Figure 6:
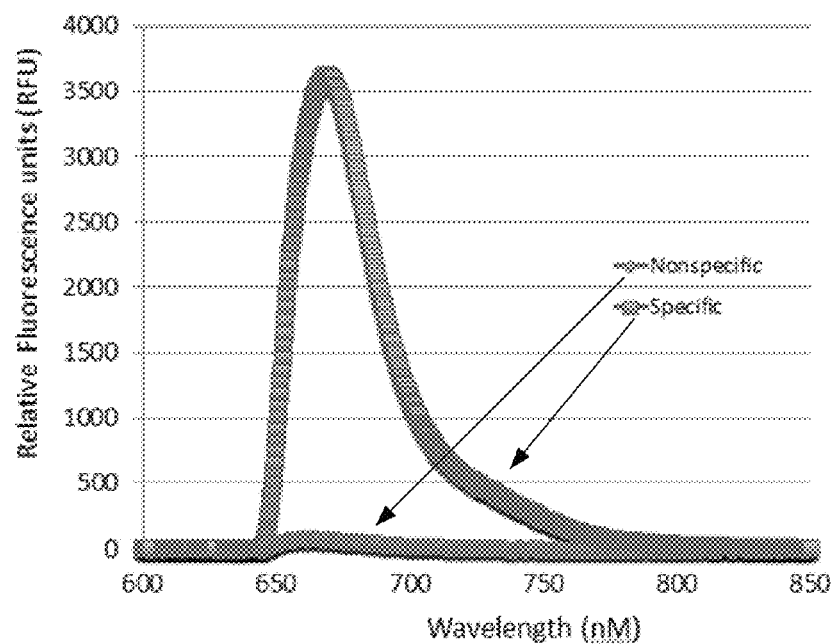
FIG. 6 is a graph illustrating detection of mycobactin T by insertion assay using fluorescent-labeled anti-mycobactin T antibody as a reporter. A known concentration of mycobactin T (57 µM) was spiked into bovine serum, the mycobactin T captured from the spiked serum using one embodiment of the provided lipid insertion assay (a synthetic lipid bilayer on a functionalized waveguide platform), and the amount captured measured using a fluorescent-labeled anti-mycobactin T antibody. Non-specific (background) fluorescence is also shown.

Results:

A specific fluorescence signal (FIG. 6) was observed when mycobactin T partitions into the lipid bilayer (supported on the waveguide surface) and is then detected using a fluorescently labeled mycobactin T reporter minibody.

Lipopolysaccharide (LPS) Assay:

For non-specific binding, fluorescently labeled reporter antibody (polyclonal anti-LPS antibody; ~50-100 nM) was added into the flow cell and incubated for 5 minutes. The flow cell was then rinsed with ~2 ml of PBS. The background (non-specific) spectrum was collected and recorded.

Standard LPS (at different concentrations, diluted in PBS or bovine/human serum) was added into the flow cell and was incubated for 30 minutes. The flow cell was then rinsed with ~2 ml of PBS.

For specific binding, fluorescently labeled reporter antibody (polyclonal anti-LPS antibody; ~50-100 nM) was added into the flow cell and incubated for 5 minutes. Then the flow cell was rinsed with ~2 ml of PBS. Spectrum was collected and recorded.

Figure 7:
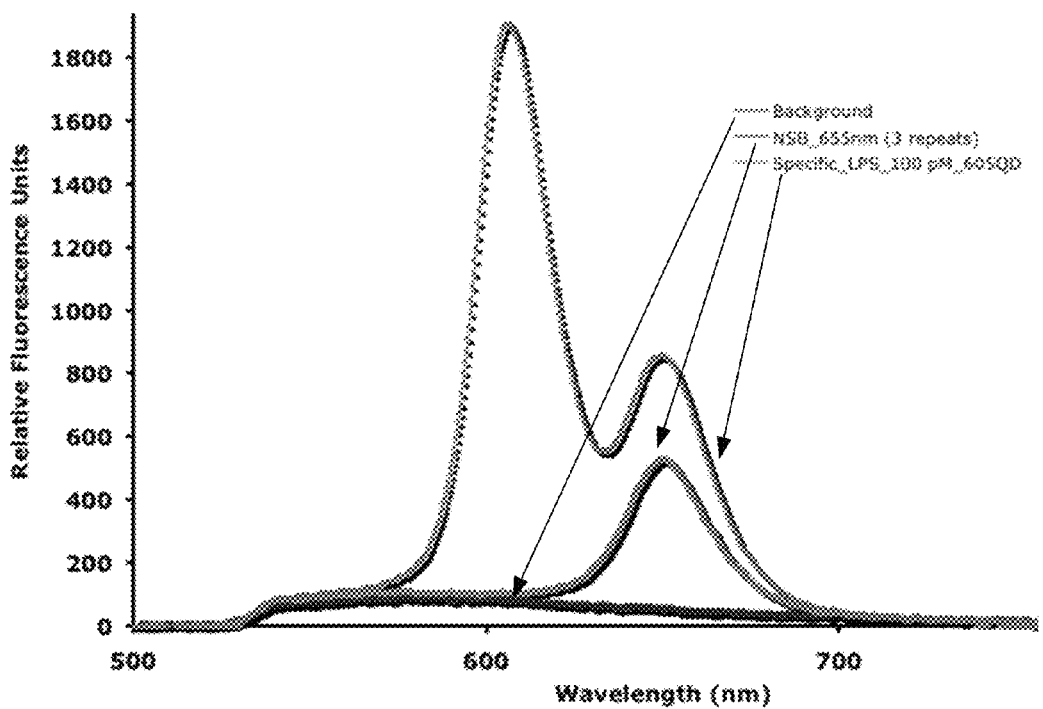
FIG. 7 is a graph illustrating detection of LPS in bovine serum by insertion assay using fluorescent-labeled anti-LPS antibody as a reporter. A known concentration of LPS (100 pM) was spiked into bovine serum, the LPS captured from the spiked serum using one embodiment of the provided lipid insertion assay (a synthetic lipid bilayer on a functionalized waveguide platform), and the amount captured measured using a fluorescent-labeled anti-LPS antibody. Background fluorescence and non-specific binding are also shown.

Results:

A specific fluorescence signal (FIG. 7) was observed when LPS partitions into the lipid bilayer (supported on the waveguide surface) and is then detected using a fluorescently labeled polyclonal LPS reporter antibody.

Lipomannan Assay:

Lipomannan is a cell wall component of *Mycobacterium bovis*, the causative agent of bovine tuberculosis. Lipomannan is distinct from lipoarabinomannan in that it lacks the arabinose (see FIG. 3A).

For non-specific binding, fluorescently labeled reporter antibody (polyclonal anti-lipomannan antibody; ~50-100 nM) was added into the flow cell and incubated for 15 minutes. The flow cell was then rinsed with ~2 ml of PBS. The background (non-specific) spectrum was collected and recorded.

Standard lipomannan (at different concentrations, diluted in PBS or bovine/human serum) was added into the flow cell and was incubated for 1 hour. The flow cell was then rinsed with ~2 ml of PBS.

For specific binding, fluorescently labeled reporter antibody (polyclonal anti-lipomannan antibody; ~50-100 nM) was added into the flow cell and incubated for 10 minutes. The flow cell was then rinsed with ~2 ml of PBS. Spectrum was collected and recorded.

Figure 8:
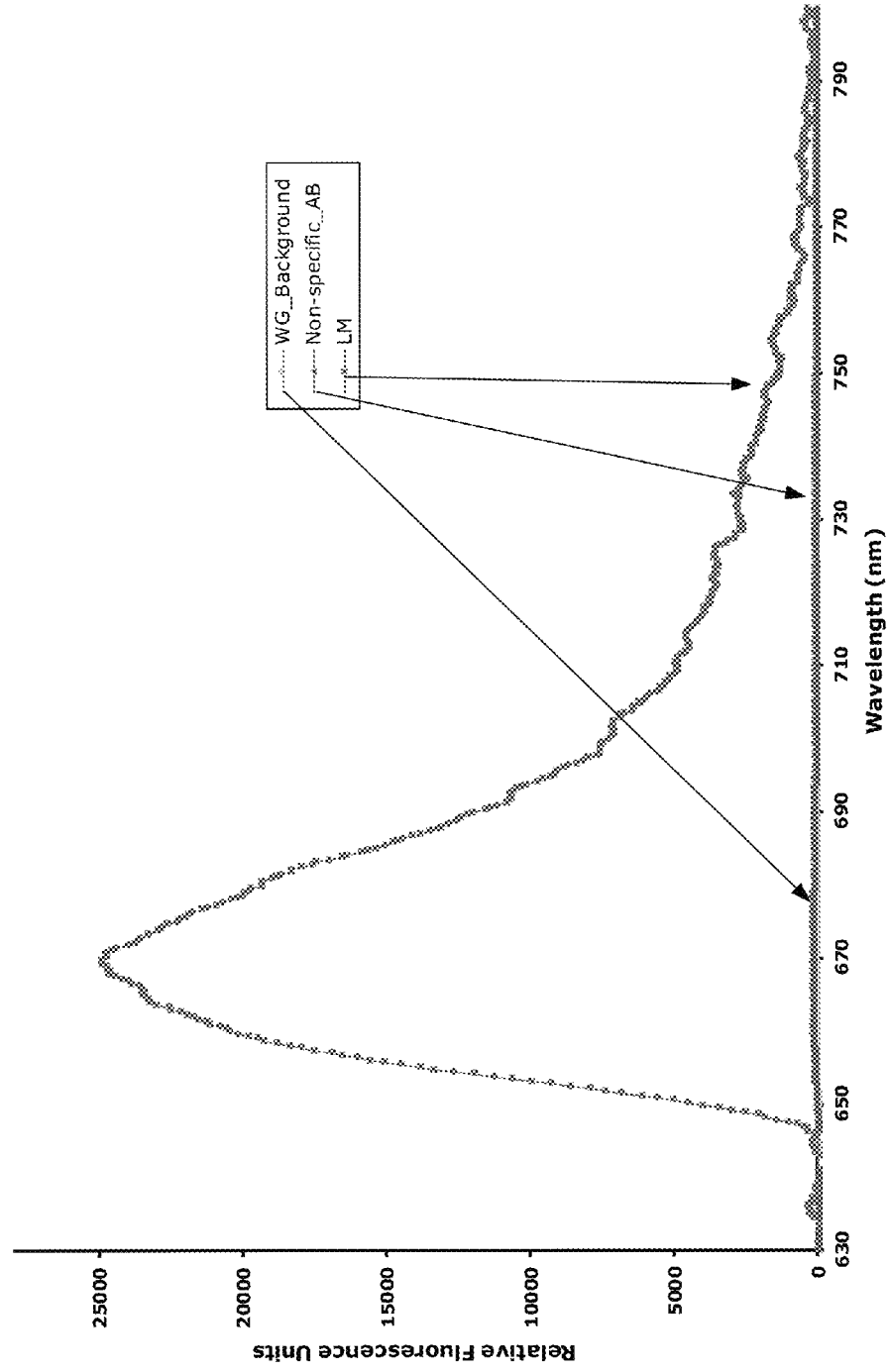
FIG. 8 is a graph illustrating detection of lipomannan in bovine serum by insertion assay using fluorescent-labeled anti-lipomannan antibody as a reporter. A known concentration of lipomannan (100 pM) was spiked into bovine serum, the lipomannan captured from the spiked serum using one embodiment of the provided lipid insertion assay (a synthetic lipid bilayer on a functionalized waveguide platform), and the amount captured measured using a fluorescent-labeled anti-lipomannan antibody (LM). Background fluorescence (WG_Background) and non-specific binding (Non-specific_AB) are also shown.

Results:

A specific fluorescence signal (FIG. 8) was observed when lipomannan partitions into the lipid bilayer (supported on the waveguide surface) and is then detected using a fluorescently labeled polyclonal lipomannan reporter antibody.

Concentration Dependence of Mycobactin T Insertion

Figure 9A:
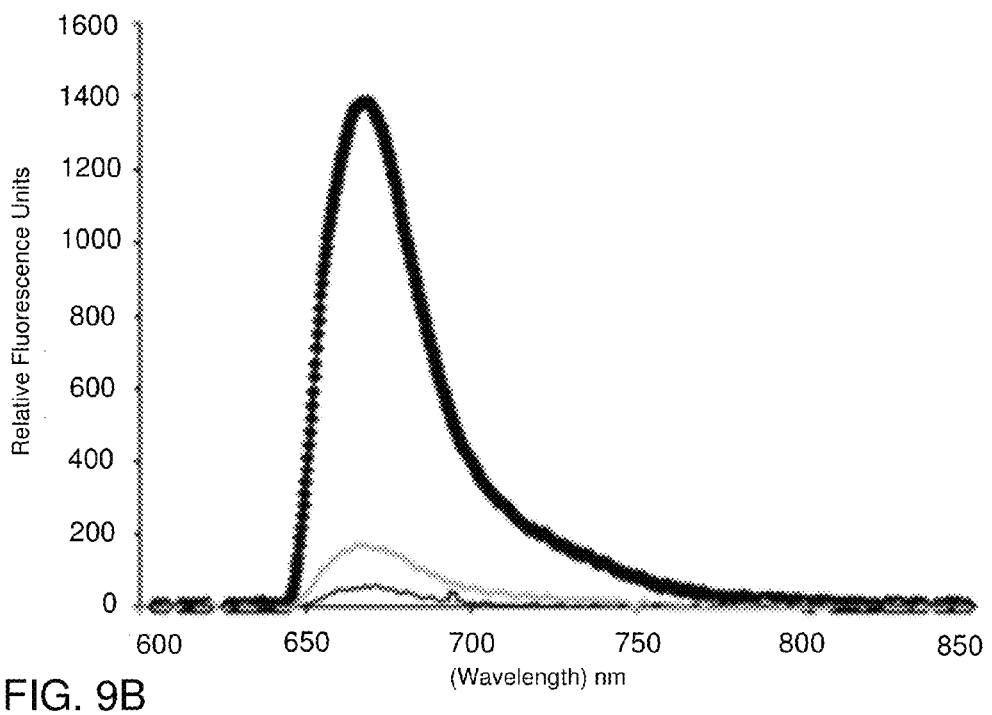
FIG. 9A is a graph showing measurement of 50 µM of mycobactin T in human serum using the membrane insertion assay. The black line indicates the waveguide-associated background; gray circles indicate non-specific background; and black triangles show specific detection of mycobactin T.
Figure 9B:
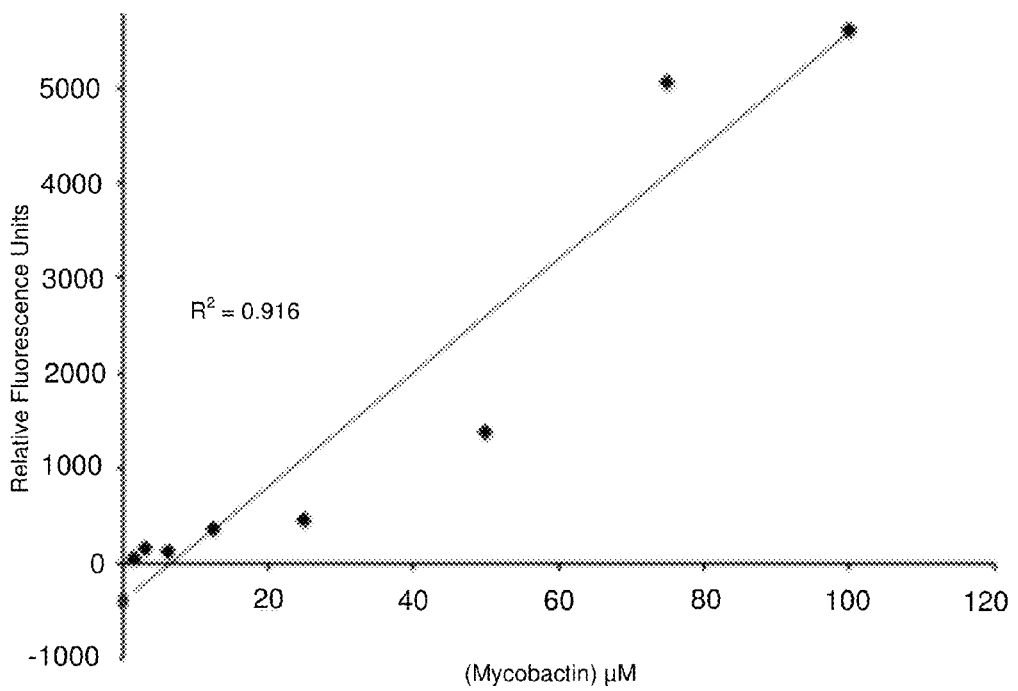
FIG. 9B is a standard curve generated on different waveguides showing a concentration-dependent increase in signal for the detection of mycobactin T in PBS.

For measurement of mycobactin T (MbT), the antigen was injected into the flow cell at various concentrations in PBS (pH7.4) or spiked in human serum (1:10 dilution) for 1 hour at room temperature, followed by addition of the Alexa Fluor 647 labeled anti-MbT reporter antibody (150 nM, 10 minutes, RT). Following washing with PBS (200 µl, 60× flow cell volume), the specific fluorescence signal associated with antigen-antibody interaction was measured using the spectrometer interface associated with the instrument. Spiking of MbT in bovine or human serum did not compromise performance, or increase non-specific binding (FIG. 9A). The limit of detection of MbT is 1 µM in serum. FIG. 9B illustrates the concentration curve generated with the detection of different concentrations of MbT using membrane insertion when measurement were performed on separate waveguides, with an $r^2$ value of 0.9. Consistent data was obtained for concentrations up to 12 µM on a single waveguide with no impedance in insertions. It has also been determined that the antibodies used in this study bind to carboxy-MbT with an equivalent binding affinity in membrane insertion assays (limit of detection is 1 µM) and do not bind to mycobactin J, enhancing the specificity of detection.

LAM Insertion Capture Time Course

For non-specific binding, fluorescently labeled reporter antibody (polyclonal LAM antibody; ~50-100 nM) was added into the flow cell and incubated for 15 minutes. The flow cell was then rinsed with ~2 ml of PBS. The background (non-specific) spectrum was collected and recorded.

Standard LAM (at 100 pM) was added in bovine/human serum and incubated for 0 hours or 7 hours in microfuge tubes. Then LAM lipid insertion assays were carried out on two separate flow cells. Serum with the LAM (incubated for indicated time points) were added into the flow cell and incubated for 1 hour. The flow cell was then rinsed with ~2 ml of PBS.

For specific binding, fluorescently labeled reporter antibody (polyclonal LAM antibody; ~50-100 nM) was added into the flow cell and incubated for 15 minutes. The flow cell was then rinsed with ~2 ml of PBS Spectra were collected and recorded.

Figure 10:
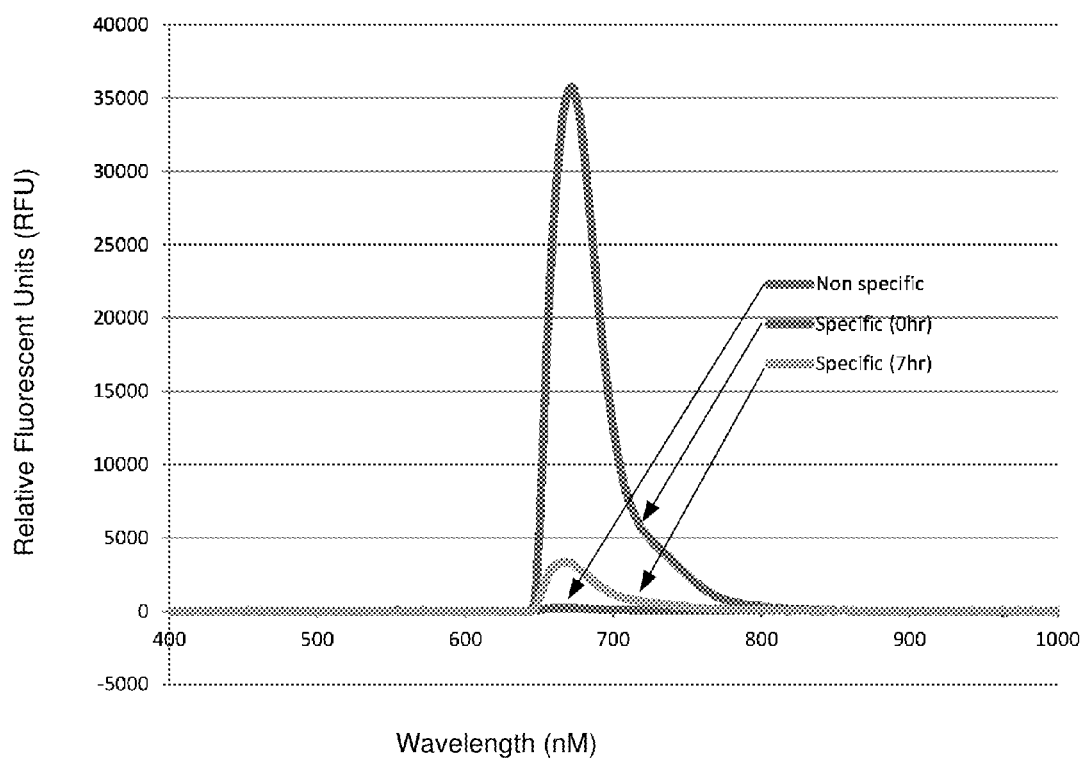
FIG. 10 is a graph showing that the amount of LAM detectable in bovine serum using a direct insertion assay with a fluorescent-labeled anti-LAM antibody as a reporter decreases with time. LAM (100 pM) was spiked into bovine serum, and the amount of LAM assayed after incubation for 0 hours and 7 hours, using a synthetic lipid bilayer on a functionalized waveguide platform. The amount of LAM captured was measured using a fluorescent-labeled anti-LAM antibody. Non-specific (background) fluorescence is also shown.

Results:

The specific fluorescence signal observed when LAM partitions into the lipid bilayer (supported on the waveguide surface) and is then detected using a fluorescently labeled polyclonal LAM reporter antibody decreased over time (FIG. 10).

Example 2: Sandwich Assays Using HDL Capture

This example provides representative methods for carrying out a sandwich assay to detect and quantify amphipathic compounds such as PAMPs that associate with HDL particles or other naturally occurring membrane structures.

Self-Assembled Monolayer (SAM) Preparation and Flow Cell Assembly

Self-assembled monolayers (SAM with 0.1% biotin) were prepared according to the procedure described by Anderson et al. (*Langmuir*, 24, 2240-2247, 2008).

To minimize non-specific binding, the bilayers were blocked for 1 hour with PBS containing 2% bovine serum albumin.

After blocking, the waveguides was washed PBS containing 0.5% bovine serum albumin and then mounted in a flow cell and mounted on the optical biosensor platform.

The laser light was in-coupled through the integrated grating and the waveguide-background was measured as a baseline metric before each experiment.

Materials:

Streptavidin is commercially available (e.g., Pierce Scientific, Rockford, Ill.; Thermo Fisher Scientific, Fremont, Calif.). Biotinylated capture antibody against ApoA1 that can recognize human HDLs was obtained from Abcam (Cambridge, Mass.). Reporter antibody for each specific biomarker (LAM/PGL-I/LPS/mycobactin; sources as above) is labeled with either Alexa-Fluor 647 or Alexa-Fluor 532, a fluorescent dye using a kit from Molecular Probes (Invitrogen, Eugene, Oreg.). Standards for the biomarkers were obtained from Tuberculosis Material consortium (Colorado State University/BEI Resources, Manassas, Va.).

Detection of LAM (or Other Biomarkers) Using Anti-ApoA1 as Capture and Biomarker of Interest as a Reporter by Sandwich Assay:

Standard LAM (at 100 pM) was added to bovine/human serum and incubated for 7 hours in a microfuge tube.

Streptavidin (~2 µM, diluted in PBS) was added into the flow cell and incubated for 10 minutes. The flow cell was then rinsed with ~2 ml of PBS.

Biotinylated capture antibody against ApoA1 (50 nM) was added into the flow cell and incubated for 10 minutes. Then the flow cell was rinsed with ~2 ml of PBS.

For non-specific binding, fluorescently labeled reporter antibody (polyclonal LAM antibody, ~50-100 nM) was added into the flow cell and incubated for 15 minutes. The flow cell was then rinsed with ~2 ml of PBS. The background (non-specific) spectrum was collected and recorded.

Standard LAM (at 100 pM) in the bovine/human serum which was incubated for 7 hours was added into the flow cell. The flow cell was then rinsed with ~2 ml of PBS.

For specific binding, fluorescently labeled reporter antibody (polyclonal LAM antibody, ~50-100 nM) was added into the flow cell and incubated for 15 minutes. The flow cell was then rinsed with ~2 ml of PBS. Spectrum was collected and recorded.

Figure 11:
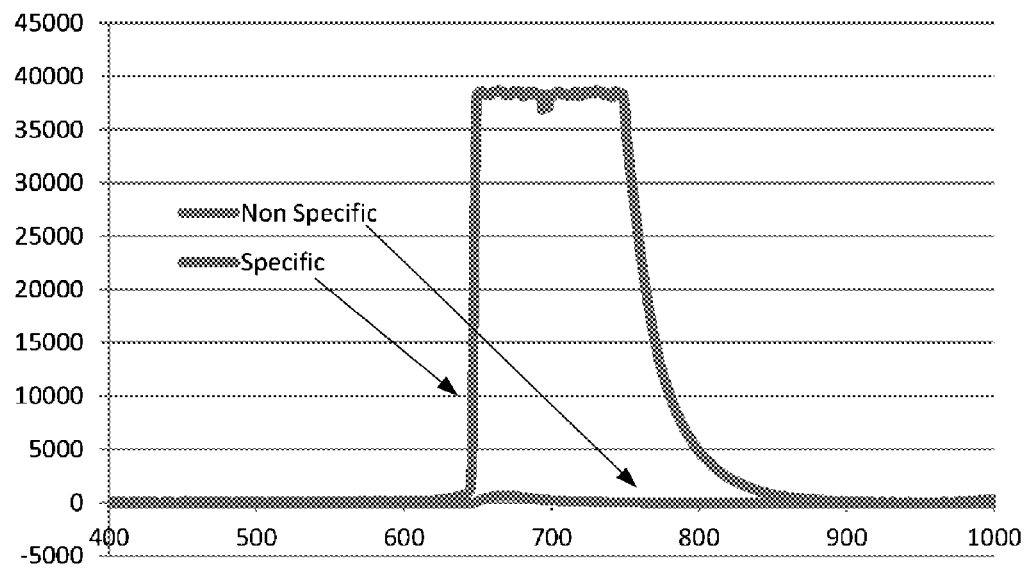
FIG. 11 is a graph illustrating detection of LAM bound to HDL in bovine serum by sandwich assay using biotinylated anti-apolipoprotein antibody as a capture and polyclonal fluorescent-labeled anti-LAM as a reporter. A sample from the 7 hour time point as illustrated in FIG. 10A was analyzed. Using the provided sandwich assay, LAM is detected bound to the HDL molecules.

Results:

Using the described sandwich assay, LAM was detected (FIG. 11) in naturally occurring HDLs after incubation of bovine serum with LAM for 7 hours.

Example 3: Detection of LAM in Patient Samples

This example illustrates that the insertion assays described herein, for instance in Example 1, are capable of detecting LAM in patient samples.

Figure 12:
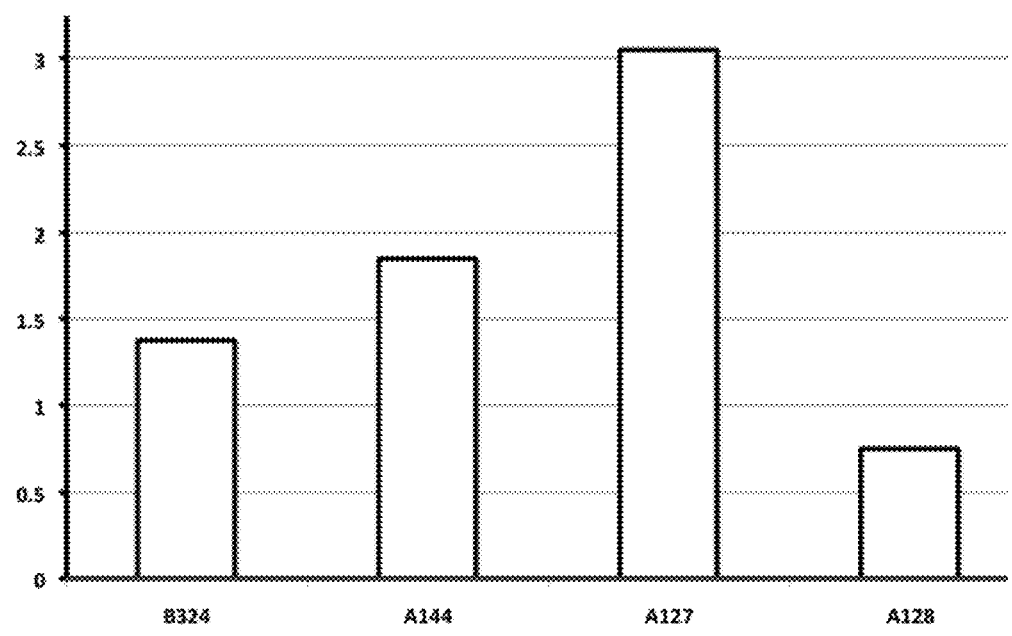
FIG. 12 is a graph illustrating detection of LAM from tuberculosis patient serum samples by lipid insertion assay using polyclonal fluorescent-labeled anti-LAM as a reporter. LAM concentrations in the tuberculosis patients serum samples were determined by comparing with the values obtained from the lipid insertion assay using a standard LAM with known concentrations.

Using methods essentially to those used in Example 1 for LAM detection, tuberculosis patient serum samples were analyzed by lipid insertion assay using polyclonal fluorescent-labeled anti-LAM as a reporter (FIG. 12). LAM concentrations in the tuberculosis patients serum samples were determined by comparing with the values obtained from the lipid insertion assay using a standard LAM with known concentrations.

Example 4: Detection of Protein Biomarkers Using Lipid Insertion Assay

This example describes detection using the lipid insertion assay of two biomarkers, culture filtrate protein 10 (CFP-10) and carcinoembryonic antigen (CEA), having a membrane spanning peptide (see FIG. 3B). The studies described below were carried out essentially as described in Example 1.

CFP-10 Assay:

For non-specific binding, fluorescently labeled reporter antibody (polyclonal CFP-10 antibody; ~50-100 nM) was added into the flow cell and incubated for 15 minutes. The flow cell was then rinsed with ~2 ml of PBS. The background (non-specific) spectrum was collected and recorded.

Standard CFP-10 (at different concentrations, diluted in PBS or bovine/human serum) was added into the flow cell and incubated for 1 hour. Then the flow cell was rinsed with ~2 ml of PBS.

For specific binding, fluorescently labeled reporter antibody (polyclonal CFP-10 antibody; ~50-100 nM) was added into the flow cell and incubated for 15 minutes. The flow cell was then rinsed with ~2 ml of PBS. Spectrum was collected and recorded.

Figure 13:
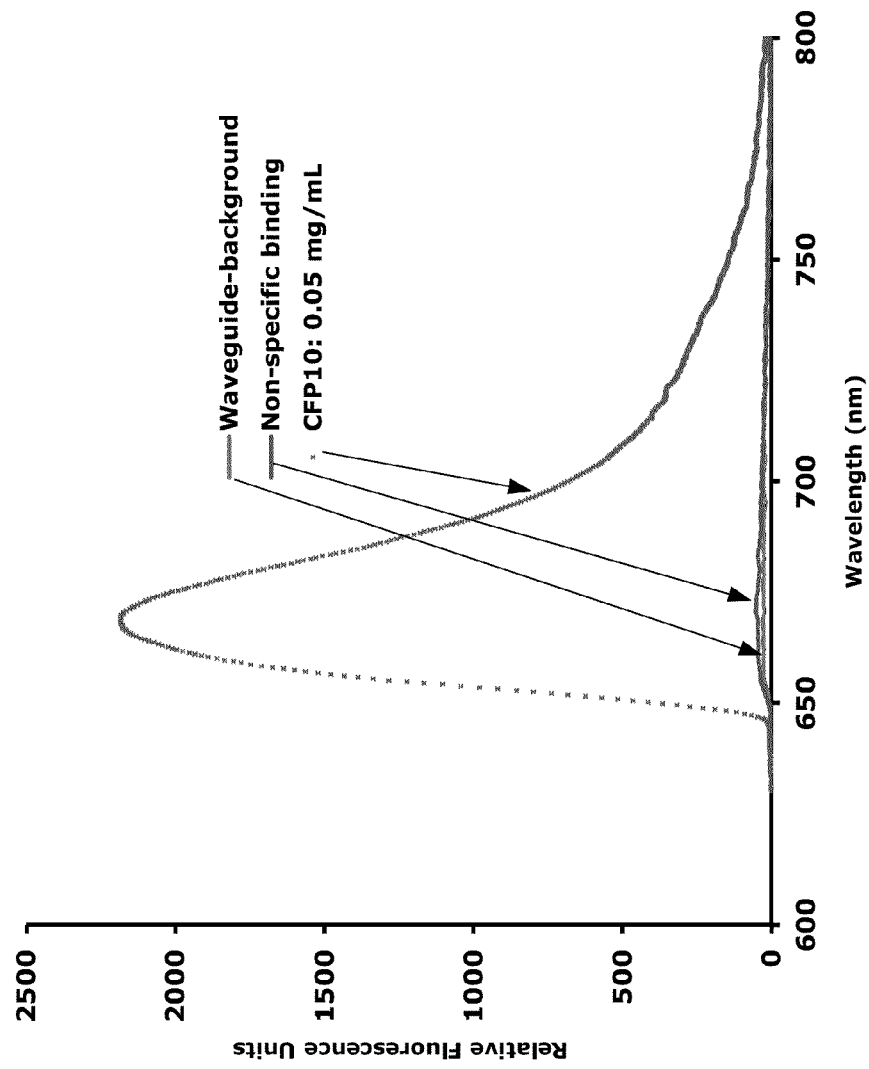
FIG. 13 is a graph illustrating detection of CFP-10 in bovine serum by insertion assay using fluorescent-labeled anti-CFP-10 antibody as a reporter. A known concentration of CFP-10 (100 pM) was spiked into bovine serum, the CFP-10 captured from the spiked serum using one embodiment of the provided lipid insertion assay (a synthetic lipid bilayer on a functionalized waveguide platform), and the amount captured measured using a fluorescent-labeled anti-CFP-10 antibody. Background fluorescence and non-specific binding are also shown.

Results:

A specific fluorescence signal (FIG. 13) was observed when CFP-10 partitions into the lipid bilayer (supported on the waveguide surface) and is then detected using a fluorescently labeled polyclonal CFP-10 reporter antibody.

Figure 14:
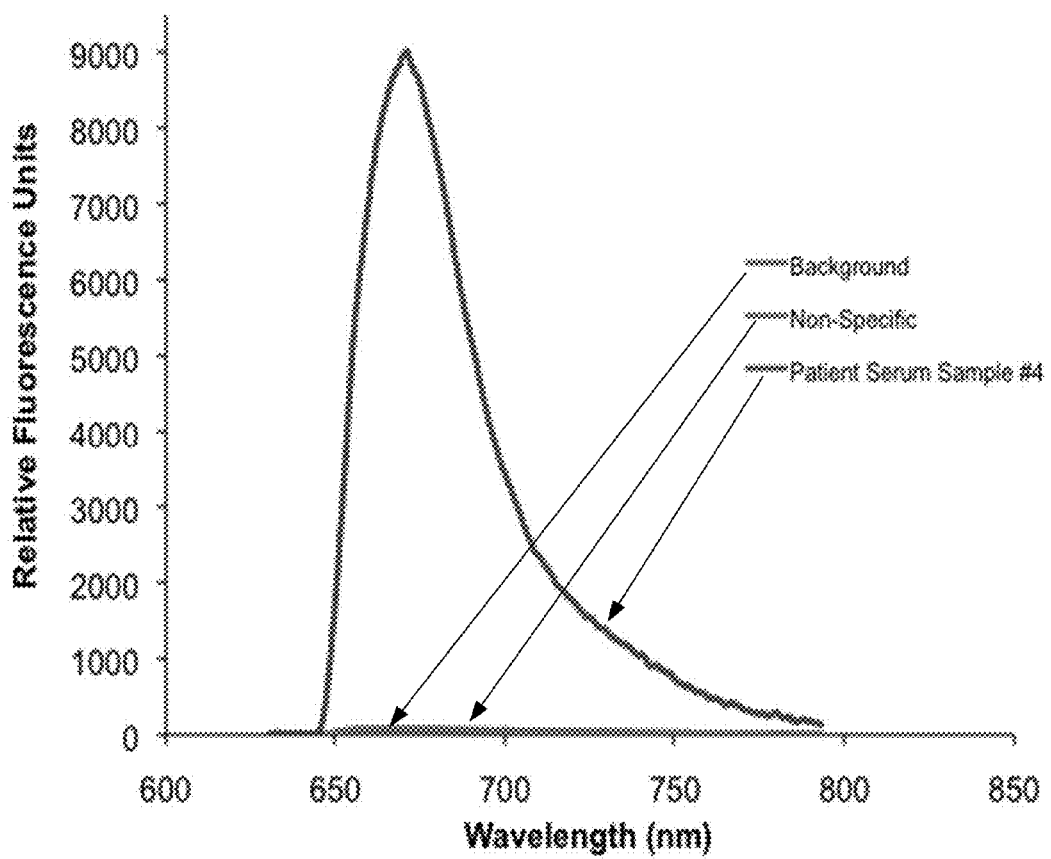
FIG. 14 is a graph illustrating detection of CEA in patient serum by insertion assay. CEA was captured from patient serum using one embodiment of the provided lipid insertion assay (a synthetic lipid bilayer on a functionalized waveguide platform), and the amount captured was measured using a fluorescent-labeled anti-CEA antibody. Background fluorescence and non-specific binding are also shown.

CEA Assay:

The CEA assay was performed using patient serum because standard recombinant CEA lacks the membrane spanning portion. The lipid insertion assay was performed using serum obtained from seven different confirmed CEA-positive patients. FIG. 14 shows the results obtained using serum from one patient. A specific fluorescence signal was observed when CEA partitions into the lipid bilayer (supported by the waveguide surface) and is then detected using a fluorescently labeled polyclonal CEA reporter antibody.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. A method of capturing and detecting at least one target moiety from a sample, which target moiety is characterized by having a lipophilic portion of sufficient size and chemical composition whereby the lipophilic portion of the at least one target moiety partially inserts into a lipid assembly that is supported on a waveguide surface, the method comprising:

(a) exposing the lipid assembly supported on the waveguide surface to the sample for sufficient time for the at least one target moiety, if present in the sample, to partially insert into the lipid assembly, wherein the at least one target moiety is exposed at the surface of the lipid assembly following partial insertion of the lipophilic portion, wherein the lipid assembly is selected from the group consisting of a substantially planar lipid structure, a vesicle, a liposome, a nanodisc, a bicelle or a micelle;

(b) contacting the lipid assembly having the exposed at least one target moiety with a fluorescently labelled antibody specific for the at least one target moiety, thereby capturing the at least one target moiety; and (c) detecting the fluorescently labelled antibody, thereby detecting the at least one target moiety.

2. The method of claim 1, wherein the substantially planar lipid structure is selected from the group consisting of a supported lipid bilayer (SLB), a tethered bilayer lipid membrane (t-BLM), a self-assembled monolayer (SAM), or a combination thereof.

3. The method of claim 1, wherein the vesicle is selected from the group consisting of a multilamellar vesicle, unilamellar vesicle, or a mixture thereof.

4. The method of claim 1, further comprising separating the captured at least one inserted target moiety from the lipid assembly.

5. The method of claim 4, further comprising characterizing the at least one target moiety by at least one of mass spectroscopy, chromatography, nuclear magnetic resonance (NMR), electrophoresis, Toll-like receptor (TLR) activity assay, and nitric oxide dioxygenase (NOD) activity assay.

6. The method of claim 1, wherein the at least one target moiety is a bacterial pathogen associated molecular pattern (PAMP) molecule selected from the group consisting of culture filtrate protein 10 (CFP-10), di-acyl lipopeptide, flagellin, lipoteichoic acid, lipid A, lipoarabinomannan (LAM), lipomannan, lipopolysaccharide (LPS), mycobactin T, peptidoglycan, phenolic glycolipid I (PGL-I), and tri-acyl lipopeptide.

7. The method of claim 1, wherein at least one target moiety is an amphiphile.

8. The method of claim 7, wherein the amphiphile is LAM, LPS, lipomannan, mycobactin T, cardiolipin or PGL-I.

9. The method of claim 1, wherein the at least one target moiety is a protein comprising a membrane spanning peptide selected from the group consisting of CFP-10 and carcinoembryonic antigen (CEA).

10. A method of assessing disease state in a first subject, comprising, taking a first biological sample from the first subject;

capturing and detecting a level of at least one PAMP molecule in the first biological sample from the first subject by performing the method of claim 6, thereby establishing a test PAMP profile;

comparing the level of the at least one target moiety of the test PAMP profile for the first biological sample from the first subject with a second PAMP profile, wherein said second PAMP profile is from a second sample, the second sample is a sample selected from the group consisting of:

a second biological sample taken from the first subject at a different time point than the first biological sample, and a biological sample taken from a second subject; and making an assessment of disease state of the first subject based on differences or similarities between the test PAMP profile and the second PAMP profile.

* * * * *